(12) United States Patent
Muchowski et al.

(10) Patent No.: US 8,466,182 B2
(45) Date of Patent: Jun. 18, 2013

(54) SMALL MOLECULE INHIBITORS OF KYNURENINE-3-MONOOXYGENASE

(75) Inventors: Paul J. Muchowski, Sunnyvale, CA (US); Joseph M. Muchowski, Westbank (CA); Robert Schwarcz, Baltimore, MD (US); Paolo Guidetti, Baltimore, MD (US)

(73) Assignees: The J. David Gladstone Institutes, A Testamentary Trust Established Under The Will Of J. David Gladstone, San Francisco, CA (US); University of Maryland, Baltimore, Baltimore, MD (US)

( * ) Notice: Subject to any disclaimer, the term of this patent is extended or adjusted under 35 U.S.C. 154(b) by 50 days.

(21) Appl. No.: 13/287,776

(22) Filed: Nov. 2, 2011

(65) Prior Publication Data

US 2012/0046324 A1 Feb. 23, 2012

Related U.S. Application Data

(62) Division of application No. 11/840,145, filed on Aug. 16, 2007, now Pat. No. 8,071,631.

(60) Provisional application No. 60/838,446, filed on Aug. 16, 2006.

(51) Int. Cl.
| | | |
|---|---|---|
| A61K 31/40 | (2006.01) |
| A61K 31/415 | (2006.01) |
| A61K 31/4168 | (2006.01) |
| A61K 31/4196 | (2006.01) |
| A61K 31/421 | (2006.01) |
| A61K 31/4245 | (2006.01) |
| C07D 207/34 | (2006.01) |
| C07D 231/38 | (2006.01) |
| C07D 233/88 | (2006.01) |
| C07D 249/14 | (2006.01) |
| C07D 261/14 | (2006.01) |
| C07D 263/48 | (2006.01) |
| C07D 271/07 | (2006.01) |
| C07D 275/03 | (2006.01) |
| C07D 285/135 | (2006.01) |
| C07D 285/08 | (2006.01) |

(52) U.S. Cl.
USPC ........... 514/363; 514/364; 514/372; 514/377; 514/378; 514/383; 514/426; 548/214; 548/233; 548/246; 548/264.8; 548/331.1; 548/372.1; 548/128; 548/131; 548/557

(58) Field of Classification Search
None
See application file for complete search history.

(56) References Cited

U.S. PATENT DOCUMENTS

| | | |
|---|---|---|
| 2,921,066 A | 1/1960 | Worffel et al. |
| 3,010,872 A | 11/1961 | Worffel et al. |
| 4,107,288 A | 8/1978 | Oppenheim et al. |
| 5,145,684 A | 9/1992 | Liversidge et al. |
| 5,856,347 A | 1/1999 | Hashiguchi et al. |
| 5,877,193 A | 3/1999 | Cesura et al. |
| 5,958,910 A | 9/1999 | Cesura et al. |
| 6,191,170 B1 | 2/2001 | Medina |
| 6,207,709 B1 | 3/2001 | Varasi et al. |
| 6,583,161 B1 | 6/2003 | Medina |
| 6,645,909 B2 | 11/2003 | Fujita et al. |
| 7,074,788 B2 * | 7/2006 | Kurz et al. ................. 514/236.2 |
| 7,173,030 B2 | 2/2007 | Pyring et al. |
| 7,183,276 B2 | 2/2007 | Sakai et al. |
| 7,727,977 B2 * | 6/2010 | Autier et al. ................. 514/183 |
| 7,994,338 B2 | 8/2011 | Muchowski et al. |
| 8,071,631 B2 | 12/2011 | Muchowski et al. |
| 2003/0130258 A1 | 7/2003 | Kurz et al. |
| 2005/0009821 A1 | 1/2005 | Pyring et al. |
| 2005/0085518 A1 | 4/2005 | Dai et al. |
| 2006/0052456 A1 | 3/2006 | Autier et al. |
| 2006/0142358 A1 | 6/2006 | Autier et al. |
| 2007/0066614 A1 | 3/2007 | Pyring et al. |
| 2008/0070905 A1 | 3/2008 | Muchowski et al. |
| 2012/0022052 A1 | 1/2012 | Muchowski et al. |

FOREIGN PATENT DOCUMENTS

| | | |
|---|---|---|
| DE | 11 21 052 | 1/1962 |
| DE | 12 49 869 B | 9/1967 |
| EP | 0 610 653 A1 | 8/1994 |
| EP | 0 790 057 | 8/1997 |
| EP | 0 819 681 A2 | 1/1998 |
| EP | 1277729 * | 1/2003 |
| GB | 905 369 | 9/1962 |

(Continued)

OTHER PUBLICATIONS

Silverman, Richard B., "The Organic Chemistry of Drug Design and Drug Action", Second Edition, Elsevier Academic Press: New York, 2004, Section E.4 "Bioisosterism", pp. 29-34.*

Scozzafava, Andrea et al., "Carbonic Anhydrase Inhibitors. Preparation of Potent Sulfonamides Ihnibitors Incorporating Bile Acid Tails", Bioorganic & Medicinal Chemistry Letters, 12(12), 1551-1557, 2002.*

Registry No. 9029-61-2, entered into Registry file on STN on Nov. 16, 1984.*

Chemical Abstracts Registry No. 371930-29-9, indexed in the Registry file on STN CAS Online Nov. 27, 2001.

(Continued)

Primary Examiner — Michael Barker
(74) Attorney, Agent, or Firm — Foley & Lardner LLP

(57) ABSTRACT

The present invention relates to compounds of Formula I below and their tautomers or pharmaceutically acceptable salts, compositions and methods of uses thereof.

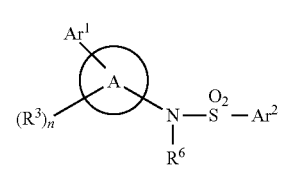

17 Claims, No Drawings

FOREIGN PATENT DOCUMENTS

| | | | |
|---|---|---|---|
| JP | 2003-292485 A | 10/2003 | |
| WO | WO-90/09787 A1 | 9/1990 | |
| WO | WO-93/05014 | 3/1993 | |
| WO | WO-99/28306 | 10/1999 | |
| WO | WO-99/28309 | 10/1999 | |
| WO | WO-03/044000 | 5/2003 | |
| WO | WO-03/072554 A1 | 9/2003 | |
| WO | WO-2004/103980 A1 | 12/2004 | |
| WO | WO 2005/005421 | * | 1/2005 |
| WO | WO-2005/013914 A2 | 2/2005 | |
| WO | WO-2005/079790 | 9/2005 | |
| WO | WO-2005/103022 | 11/2005 | |
| WO | WO 2007/039175 | * | 4/2007 |
| WO | WO-2008/022286 A2 | 2/2008 | |

OTHER PUBLICATIONS

Chemical Abstracts Registry No. 565171-37-1, indexed in the Registry file on STN CAS Online Aug. 12, 2003.

European Extended Search Report for Application No. 11189793.0, Mailed Dec. 19, 2011.

An English translation of JP 2003-292485, Oct. 15, 2003.

Bell, F. "Investigations in the Diphenyl Series. Part IX. Further Experiments with Sulphonamides" Journal of the Chemical Society, Chemical Society, Letchworth; GB LNKD-DOI:10.1039/JR9300001071, Jan. 1, 1930, pp. 1071-1077, XP009018773 ISSN: 0368-1769.

Bouchain, G. et al. "Development of Potential Antitumor Agents. Synthesis and Biological Evaluation of a New Set of Sulfonamide Derivates as Histone Deacetylase Inhibitors" Journal of Medicinal Chemistry, American Chemical Society, Washington, US LNKD-DOI:10.1021/JM020377A, vol. 46, Jan. 1, 2003, pp. 820-830, XP002278212. ISSN: 0022-2623.

Bouchain, G. et al. "Novel hydroxamate and anilide derivatives as potent histone deacetylase inhibitors: Synthesis and antiproliferative evaluation" Current Medicinal Chemistry, Bentham Science Publishers BV, BE LNKD-DOI:10.2174/0929867033456585, vol. 10, No. 22, Jan. 1, 2003, pp. 2359-2372, XP002480700, ISSN: 0929-8673.

Case, F. H. "Nitration of certain halo biphenyls. IV. Nitro derivatives of 3-bromobiphenyl" Journal of the American Chemical Society, Coden: JACSAT; ISSN: 0002-7863, vol. 67, 1945, pp. 116-121, XP002590239.

Chemical Abstracts Registry No. 402767-36-6, indexed in the file Registry on STN Mar. 25, 2002.

Chemical Abstracts Registry No. 894531-35-2, indexed in the file Registry on STN Jul. 19, 2006.

Dhanoa, D.S., et al. "Serine Proteases-Directed Small Molecule Probe Libraries" Medicinal Chemistry Research, Birkhaeuser, Boston, US, vol. 8, No. 4/05, Jan. 1, 1998, pp. 187-205, XP009016618, ISSN: 1054-2523.

El-Hewehi, Zaki. et al. "Sulfonic acid derivatives. III. Preparation, composition, and insecticide activity of sulfonamides" Journal Fuer Praktische Chemie (LEIPZIG), 34(5-6), 218-42 Coden: JPCEAO; ISSN: 0021-8383, 1966, XP009135712.

Erickson et al., A Radiometric Assay for Kynurenine 3-Hydroxylase Based on the Release of 3H2O During Hydroxylation of L-[3,5-3H]-Kynurenine, Anal. Biochem. 1992, 205, 257-262.

Finn, P.W. et al. "Novel Sulfonamide Derivatives as Histone Deacetylase" Helvetica Chimica Acta, Verlag Helvetica Chimica Acta, Basel, CH LNKD-DOI:10.1002/HLCA.200590129, vol. 88, Jul. 1, 2005, pp. 1630-1657, XP002367316. ISSN: 0018-019X.

Ingle, D.B. et al. "Synthesis of 2-sulfanilamidothiazole derivatives and their antibacterial activity". Database CA [Online] Chemical Abstracts Service, Columbus, Ohio, US; XP002549764 retrieved from STN, Database accession No. 1979:38829.

Ingle, D.B. et al. "Synthesis of 2-sulfanilamidothiazole derivatives and their antibacterial activity". Database CA [Online] Chemical Abstracts Service, Columbus, Ohio, US; XP002549764 retrieved from STN, Database accession No. 1979:38829, J. Indian Chem. Soc. 55(1):50-51 (1978).

Joshi, K.C. et al. "Organic Pesticides. Part X. Preparation of Some 2-Amino-4-aryl-5-alkylthiazoles and Related Compounds, N-Substituted Aminothiazoles and their Mercurials, and 2-p-Fluor4o-phenylimino-4-thiazolidone and its Condensation Products" Journal of the Indian Chemical Society, 39(2):121-128 (1962); XP000571711.

Joshi, K.C. et al. "Organic Pesticides. Part X. Preparation of Some 2-Amino-4-aryl-5-alkylthiazoles and Related Compounds, N-Substituted Aminothiazoles and their Mercurials, and 2-p-Fluoro-phenylimino-4-thiazolidone and its Condensation Products" Journal of the Indian Chemical Society, The Indian Chemical Society, Calcutta, IN, vol. 39, No. 2, Jan. 1, 1962, pp. 121-128, XP000571711.

Khan, R.H. et al. "Synthesis of Fluoroarylthiazoles and Related Compounds as Possible Fungicides" Agricultural and Biological Chemistry, Japan Soc. for Bioscience, Biotechnology and Agrochem, Tokyo, JP, vol. 40, No. 6, Jan. 1, 1976, pp. 1129-1135, XP001026659.

Khan, R.H. et al. "Synthesis of Fluoroarylthiazoles and Related Compounds as Possible Fungicides", Agr. Biol. Chem. 40(6):1129-1135 (1976); XP001026659.

Neidlein et al., Chemical Abstacts, 69:96590, 1968.

R. Schwarcz and R. Pellicciari, "Manipulation of Brain Kynurenines; Glial Targets, Neuronal Effects, and Clinical Opportunities," The Journal of Pharmacology and Experimental Therapeutics, 303(1),1-10 (2002).

Raju, B. et al. "Solid Phase Synthesis of Sulfonamides Using a Carbamate Linker" Tetrahedron Letters, Elsevier, Amsterdam, NL LNKD-DOI:10.1016/50040-4039(97)00652-7, vol. 38, No. 19, May 12, 1997, pp. 3373-3376, XP004061429, ISSN: 0040-4039.

Richter, A. et al. "The kynurenine 3-hydroxylase inhibitor Ro 61/8048 improves dystonia in a genetic model of paroxysmal dyskinesia." European Journal of Pharmacology, 478 (2003) 47-52.

Richter, et al. "The kynurenine 3-hydroxylase inhibitor Ro 61-8048 improves dystonia in a genetic model of paroxysmal dyskinesia." European Journal of Pharmacology, 478 (2003) 47-52.

Rover, et al., J. Med. Chem. 1997, 40, 4378-4385.

Somaglino, J. C. "Sulfonamides" Database CA [Online] Chemical Abstracts Service, Columbus, Ohio, US; 1941, XP002590240.

* cited by examiner

SMALL MOLECULE INHIBITORS OF KYNURENINE-3-MONOOXYGENASE

CROSS-REFERENCE TO RELATED APPLICATION

This application is a divisional of U.S. application Ser. No. 11/840,145, filed Aug. 16, 2007, which claims benefit under 35 U.S.C. §119 (e) of U.S. Provisional Application Ser. No. 60/838,446, filed Aug. 16, 2006, which are hereby incorporated by reference in their entirety.

FIELD OF THE INVENTION

This invention relates generally to benzenesulfonamide compounds and their use as inhibitors of kynurenine-3-monooxygenase.

BACKGROUND OF THE INVENTION

Tryptophan is metabolized in mammals via the kynurenine pathway to yield three neuroactive substances, 3-hydroxykynurenine, kynurenic acid and quinolinic acid. Kynurenic acid has neuroprotective activities in vivo while 3-hydroxykynurenine and quinolinic acid are neurotoxic. Studies have shown that 3-hydroxykynurenine and quinolinic acid are causative or contribute to delayed neurological damages and are associated with a variety of human diseases including neurodegenerative disorders and psychiatric diseases. Pharmacological intervention aimed at blocking 3-hydroxykynurenine and quinolinic acid synthesis and/or increasing kynurenic acid formation have been attempted in treatment of neurological diseases and their peripheral indications, such as diabetes.

Kynurenine-3-monooxygenase (KMO) is an enzyme in the tryptophan degradation pathway that catalyzes the conversion of kynurenine into 3-hydroxykynurenine which is a precursor of the neurotoxin quinolinic acid. Therefore, compounds which act as inhibitors of KMO are of particular interest since they block the metabolism toward quinolinic acid and at the same time, increase the formation of neuroprotective metabolite kynurenic acid.

Inhibitors of KMO have been known in the art. For example, U.S. Pat. No. 5,877,193 describes N-(4-arylthiazol-2-yl)-sulfonamide derivatives for treating neurodegenerative disorders resulting from an activation of the immune system.

There remains a need for compounds that are effective inhibitors of KMO and can be used in treating neurodegenerative disorders. Compounds that inhibit KMO and can thus be used to treat and prevent KMO-associated disorders including neurodegenerative disorders are provided herein.

SUMMARY OF THE INVENTION

This invention is directed to novel compounds, pharmaceutical compositions and methods of using the compounds to inhibit KMO.

In one aspect of the invention, there are provided compounds of Formula I:

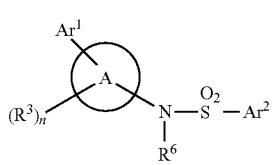

wherein:
A is selected from the group consisting of aryl and heteroaryl;
$Ar^1$ and $Ar^2$ are independently selected from the group consisting of aryl, substituted aryl, heteroaryl, and substituted heteroaryl;
$R^3$ is selected from the group consisting of hydrogen, alkyl, substituted alkyl, alkoxy, substituted alkoxy, halo, amino, substituted amino, alkylthio, substituted alkylthio, substituted sulfonyl, substituted sulfinyl, aryl, substituted aryl, heteroaryl, and substituted heteroaryl;
$R^6$ is selected from the group consisting of hydrogen, alkyl, substituted alkyl, aryl, substituted aryl, heteroaryl, and substituted heteroaryl;
n is an integer from 0 to 3;
or their tautomers and/or a pharmaceutically acceptable salt thereof,
with the proviso that A is not 1,3-thiazol-2-yl.

In some embodiments of the invention, there are provided compounds of Formula II:

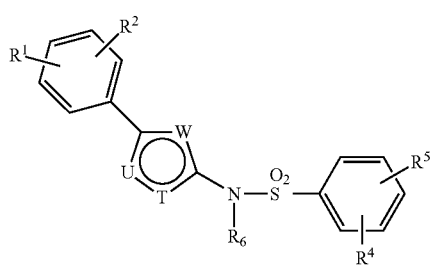

wherein:
T and W independently are selected from the group consisting of N, $NR^3$, S, S(O), $S(O)_2$, O, and $CR^5$ and U is selected from the group consisting of N, $NR^3$, S, S(O), $S(O)_2$, and O with the proviso that no more than one of T, U, and W are S, S(O), $S(O)_2$, and O;
$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;
$R^3$ is selected from the group consisting of hydrogen, alkyl, substituted alkyl, alkoxy, substituted alkoxy, halo, amino, substituted amino, alkylthio, substituted alkylthio, substituted sulfonyl, substituted sulfinyl, aryl, substituted aryl, heteroaryl, and substituted heteroaryl;
$R^4$ and $R^5$ are independently selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl; and
$R^6$ is selected from the group consisting of hydrogen, alkyl, substituted alkyl, aryl; substituted aryl, heteroaryl and substituted heteroaryl;
or their tautomers and/or a pharmaceutically acceptable salt thereof.

In a particular embodiment, there are provided compounds of Formula IIa or their tautomers and/or a pharmaceutically acceptable salt thereof:

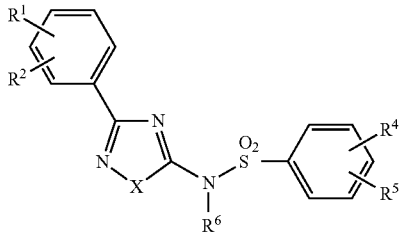

IIa wherein X is S or NR$^9$ where R$^9$ is alkyl or substituted alkyl; and R$^1$, R$^2$, R$^4$, R$^5$, and R$^6$ are as defined herein.

In another particular embodiment, there are provided compounds of Formula IIb or their tautomers and/or a pharmaceutically acceptable salt thereof:

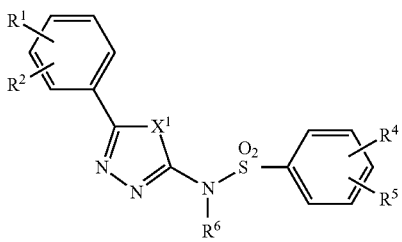

IIb wherein X$^1$ is S or NH; and R$^1$, R$^2$, R$^4$, R$^5$, and R$^6$ are as defined herein.

In another particular embodiment, there are provided compounds of Formula IIc or their tautomers and/or a pharmaceutically acceptable salt thereof:

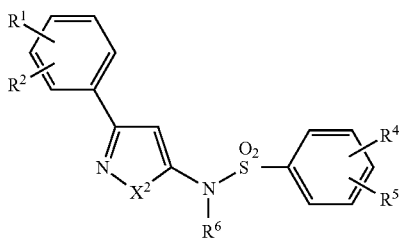

IIc wherein X$^2$ is O or NR$^9$ where R$^9$ is alkyl or substituted alkyl; and R$^1$, R$^2$, R$^4$, R$^5$, and R$^6$ are as defined herein.

In another particular embodiment, there are provided compounds of Formula IId or their tautomers and/or a pharmaceutically acceptable salt thereof:

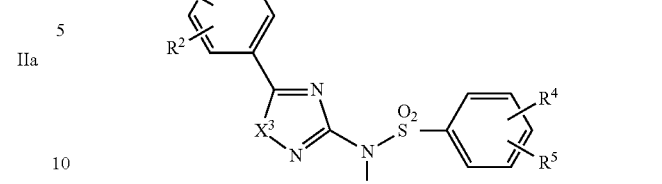

IId wherein X$^3$ is S or NR$^9$ where R$^9$ is alkyl or substituted alkyl; and R$^1$, R$^2$, R$^4$, R$^5$, and R$^6$ are as defined herein.

In another particular embodiment, there are provided compounds of Formula IIe or their tautomers and/or a pharmaceutically acceptable salt thereof:

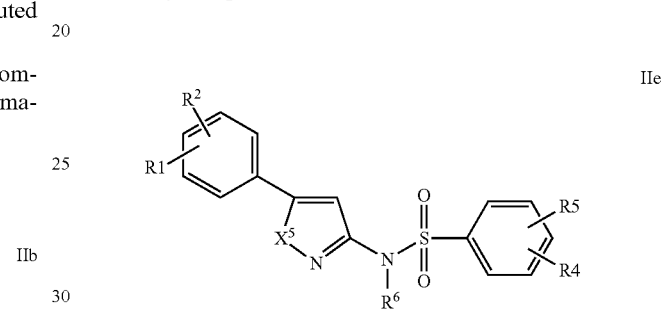

IIe wherein X$^5$ is O, S, NH, or NR$^3$; and R$^1$, R$^2$, R$^3$, R$^4$, R$^5$, and R$^6$ are as defined herein.

In another particular embodiment, there are provided compounds of Formula IIf or their tautomers and/or a pharmaceutically acceptable salt thereof:

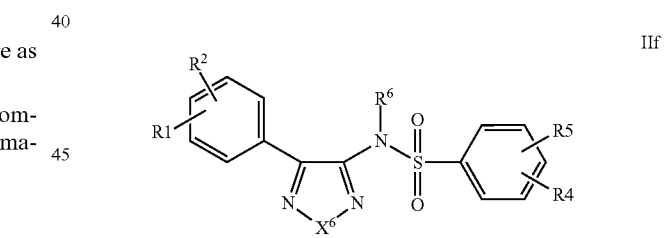

IIf wherein X$^6$ is O, S, NH, or NR$^3$; and R$^1$, R$^2$, R$^3$, R$^4$, R$^5$, and R$^6$ are as defined herein.

In another particular embodiment, there are provided compounds of Formula IIg or their tautomers and/or a pharmaceutically acceptable salt thereof:

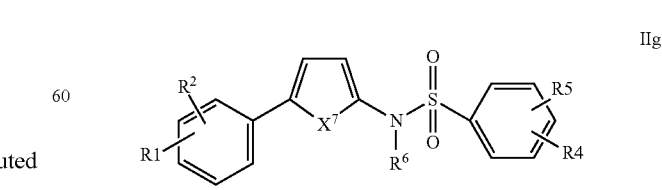

IIg wherein X$^7$ is O, S, NH, or NR$^3$; and R$^1$, R$^2$, R$^3$, R$^4$, R$^5$, and R$^6$ are as defined herein.

In some embodiments of the invention, there are provided compounds of Formula III:

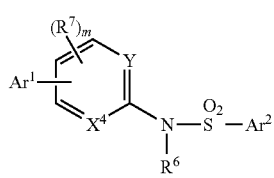

III $X^4$ and Y are independently selected from the group consisting of N and $CR^8$;

$Ar^1$ and $Ar^2$ are independently selected from the group consisting of aryl, substituted aryl, heteroaryl, and substituted heteroaryl;

$R^6$ is selected from the group consisting of hydrogen, alkyl, substituted alkyl, aryl, substituted aryl, heteroaryl, and substituted heteroaryl;

$R^7$ is selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or 2 or more $R^7$ join to form a ring when m>1, where the ring is selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

m is an integer from 0 to 3; and $R^8$ is selected from the group consisting of hydrogen, alkyl, substituted alkyl, halo, amino, substituted amino, aryl, substituted aryl, heteroaryl, and substituted heteroaryl;

or their tautomers and/or a pharmaceutically acceptable salt thereof.

In some embodiments of the invention, there are provided compounds of Formula IIIa:

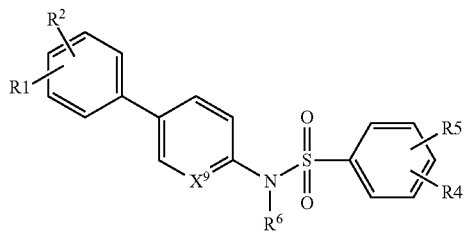

IIIa wherein $X^9$ is N or CH; and $R^1$, $R^2$, $R^4$, $R^5$, and $R^6$ are as defined herein.

In some embodiments of the invention, there are provided compounds of Formula IIIb:

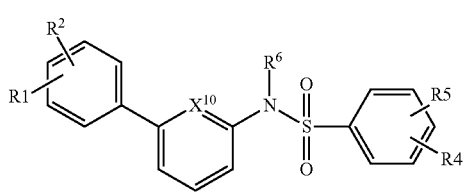

IIIb wherein $X^{10}$ is N or CH; and $R^1$, $R^2$, $R^4$, $R^5$, and $R^6$ are as defined herein.

In some embodiments of the invention, there are provided compounds of Formula IIIc:

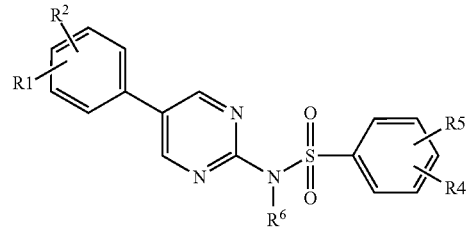

IIIc wherein $R^1$, $R^2$, $R^4$, $R^5$, and $R^6$ are as defined herein.

In some embodiments of the invention, there are provided compounds of Formula IIId:

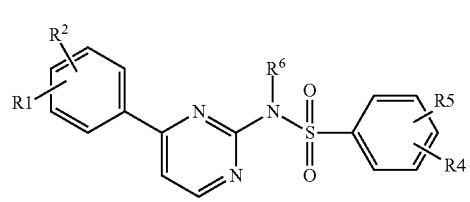

IIId wherein $R^1$, $R^2$, $R^4$, $R^5$, and $R^6$ are as defined herein.

In another aspect of the invention, the invention provides pharmaceutical compositions comprising one or more compounds of Formula I, II, IIa, IIb, IIc, IId, IIe, IIf, IIg, III, IIIa, IIIb, IIIc, or IIId and a pharmaceutically acceptable excipient.

In one of its method aspects, this invention is directed to a method for inhibiting activity of kynurenine-3-monooxygenase activity which method comprises contacting cells (including neurons/microglia/invading macrophages) with an effective amount of one or more compounds of Formula I, II, IIa, IIb, IIc, IId, IIe, IIf, IIg, III, IIIa, IIIb, IIIc, or IIId.

In another of its method aspects, this invention is directed to a method for treating a disease mediated at least in part by kynurenine-3-monooxygenase which method comprises administering to a patient an effective amount of one or more compounds of Formula I or a pharmaceutical composition comprising a pharmaceutically acceptable excipient and one or more compounds of Formula I, II, IIa, IIb, IIc, IId, IIe, IIf, IIg, III, IIIa, IIIb, IIIc, or IIId.

Diseases mediated at least in part by kynurenine-3-monooxygenase include those selected from the group consisting of Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behaviour, schizophrenia, chronic anxiety, depressive disorders, disorders of the developing or aged brain, diseases of addiction, diabetes, and complications thereof. The compounds of this invention may also influence synaptogenesis after brain injury. The compounds also may influence memory.

In another of its method aspects, this invention is directed to an article of manufacture for use to inhibit kynurenine-3-monooxygenase for treating a disease mediated at least in part by kynurenine-3-monooxygenase comprising a composition comprising a pharmaceutically acceptable excipient and compound of the Formula I, II, IIa, IIb, IIc, IId, IIe, IIf, IIg, III, IIIa, IIIb, IIIc, or IIId, as provided herein. The diseases mediated at least in part by kynurenine-3-monooxygenase are as provided herein. In one embodiment, the article of manufacture further comprises a label with instructions for using the composition to treat a disease mediated at least in part by kynurenine-3-monooxygenase.

DETAILED DESCRIPTION OF THE INVENTION

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

1. DEFINITIONS

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

Preferred substituted alkyl groups included halogenated alkyl groups and particularly halogenated methyl groups such as trifluoromethyl, difluromethyl, fluoromethyl and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{30}C(O)$alkyl, —$NR^{30}C(O)$substituted alkyl, —$NR^{30}C(O)$cycloalkyl, —$NR^{30}C(O)$substituted cycloalkyl, —$NR^{30}C(O)$alkenyl, —$NR^{30}C(O)$substituted alkenyl, —$NR^{30}C(O)$alkynyl, —$NR^{30}C(O)$substituted alkynyl, —$NR^{30}C(O)$aryl, —$NR^{30}C(O)$substituted aryl, —$NR^{30}C(O)$heteroaryl, —$NR^{30}C(O)$substituted heteroaryl, —$NR^{30}C(O)$heterocyclic, and —$NR^{30}C(O)$substituted heterocyclic wherein $R^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —$C(O)NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —$C(S)NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{30}C(O)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —$NR^{30}C(S)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—$C(O)NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —$SO_2NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—$SO_2NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —$NR^{30}$—$SO_2NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —$C(=NR^{35})NR^{33}R^{34}$ where $R^{33}$, $R^{34}$, and $R^{35}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —$NR^{30}$—C(O)O-alkyl, —$NR^{30}$—C(O)O-substituted alkyl, —$NR^{30}$—C(O)O-alkenyl, —$NR^{30}$—C(O)O-substituted alkenyl, —$NR^{30}$—C(O)O-alkynyl, —$NR^{30}$—C(O)O-substituted alkynyl, —$NR^{30}$—C(O)O-aryl, —$NR^{30}$—C(O)O-substituted aryl, —$NR^{30}$—C(O)O-cycloalkyl, —$NR^{30}$—C(O)O-substituted cycloalkyl, —$NR^{30}$—C(O)O-heteroaryl, —$NR^{30}$—C(O)O-substituted heteroaryl, —$NR^{30}$—C(O)O-heterocyclic, and —$NR^{30}$—C(O)O-substituted heterocyclic wherein $R^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but non-aromatic cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Guanidino" refers to the group —NHC(=NH)$NH_2$.

"Substituted guanidino" refers to —$NR^{36}$C(=$NR^{36}$)N($R^{36}$)$_2$ where each $R^{36}$ is independently selected from the group consisting of hydrogen, alkyl, substituted alkyl, aryl, substituted aryl, heteroaryl, substituted heteroaryl, heterocyclic, and substituted heterocyclic and two $R^{36}$ groups attached to a common guanidino nitrogen atom are optionally joined together with the nitrogen bound thereto to form a heterocyclic or substituted heterocyclic group, provided that at least one $R^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —$NO_2$.

"Oxo" refers to the atom (=O) or (—$O^-$).

"Spiro ring systems" refers to bicyclic ring systems that have a single ring carbon atom common to both rings.

"Sulfinyl" refers to the divalent group —SO—.

"Sulfonyl" refers to the divalent group —S(O)$_2$—.

"Substituted sulfonyl" refers to the group —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-$SO_2$—, phenyl-$SO_2$—, and 4-methylphenyl-$SO_2$—. Preferred substituted alkyl groups on the substituted alkyl-$SO_2$— include halogenated alkyl groups and particularly halogenated methyl groups such as trifluoromethyl, difluromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluromethyl, fluoromethyl and the like.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

2. COMPOUNDS OF THE INVENTION

This invention is directed to compounds, compositions and methods of using the compounds as inhibitors of KMO and inhibit the KMO activities in the brain.

In one aspect, the present invention provides compounds of general Formula I:

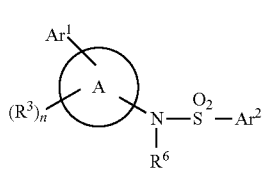

wherein:

A is selected from the group consisting of aryl and heteroaryl;

$Ar^1$ and $Ar^2$ are independently selected from the group consisting of aryl, substituted aryl, heteroaryl, and substituted heteroaryl;

$R^3$ is selected from the group consisting of hydrogen, alkyl, substituted alkyl, alkoxy, substituted alkoxy, halo, amino, substituted amino, alkylthio, substituted alkylthio, substituted sulfonyl, substituted sulfinyl, aryl, substituted aryl, heteroaryl, and substituted heteroaryl;

$R^6$ is selected from the group consisting of hydrogen, alkyl, substituted alkyl, aryl, substituted aryl, heteroaryl, and substituted heteroaryl;

n is an integer from 0 to 3;

or their tautomers and/or a pharmaceutically acceptable salt thereof, with the proviso that A is not 1,3-thiazol-2-yl.

In particular embodiments, the heteroaryl group is a 5- or 6-membered heteroaryl group.

In some embodiments, there are provided compounds of general Formula II:

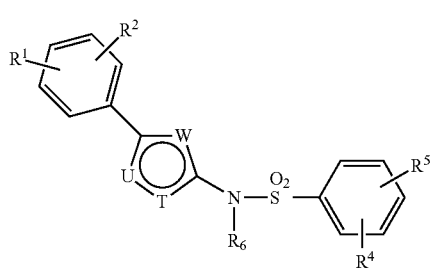

wherein:

T and W independently are selected from the group consisting of N, $NR^3$, S, S(O), $S(O)_2$, O, and $CR^3$ and U is selected from the group consisting of N, $NR^3$, S, S(O), $S(O)_2$, and O with the proviso that no more than one of T, U, and W are S, S(O), $S(O)_2$, and O;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, alkyl, substituted alkyl, alkoxy, substituted alkoxy, halo, amino, substituted amino, alkylthio, substituted alkylthio, substituted sulfonyl, substituted sulfinyl, aryl, substituted aryl, heteroaryl, and substituted heteroaryl;

$R^4$ and $R^5$ are independently selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl; and $R^6$ is selected from the group consisting of hydrogen, alkyl, substituted alkyl, aryl; substituted aryl, heteroaryl and substituted heteroaryl;

or their tautomers and/or a pharmaceutically acceptable salt thereof.

In some embodiments, one or both of $R^1$ and $R^2$ in Formula II are hydrogen, nitro, or methoxy, respectively.

In some embodiments, one or both of $R^4$ and $R^5$ in Formula II are hydrogen, methyl, or methoxy, respectively.

In some embodiments, the group

represents pyrazole, thiazole, isoxazole, thiadiazole, or triazole.

In some preferred embodiments, the compounds of the present invention are represented by Formulas IIa through IIg:

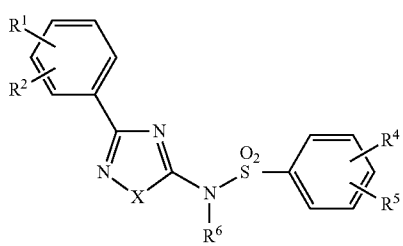

IIa

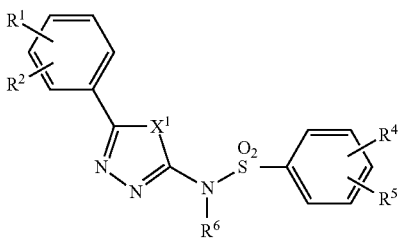

IIb

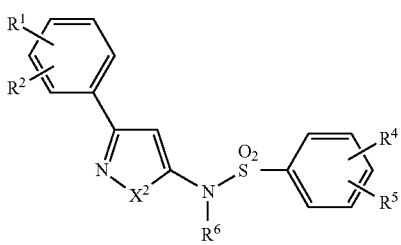

IIc

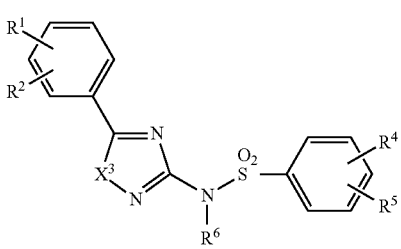

IId

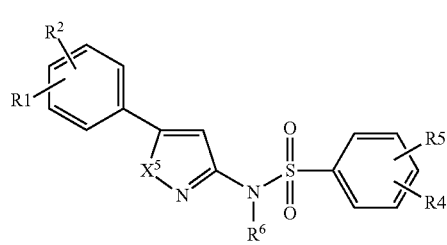

IIe

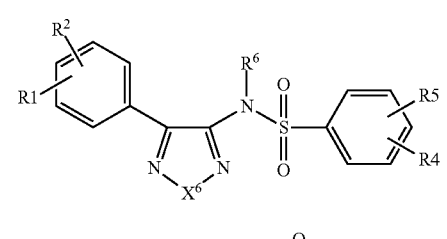

IIf

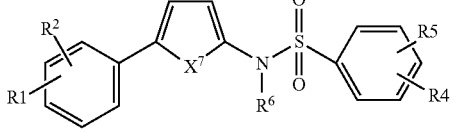

IIg

In Formulas IIa through IIg, $R^1$, $R^2$, $R^4$ and $R^5$ are independently hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring, and/or $R^4$ and $R^5$ join together to form a ring where the ring is selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

In Formulas IIa through IIg, X, $X^1$, $X^2$, $X^3$, $X^5$, $X^6$, $X^7$, and Z independently represent O, S, NH, or $NR^3$ where $R^3$ is as defined herein. In some preferred embodiments, X, $X^1$, $X^2$, $X^3$, $X^5$, $X^6$, $X^7$, and Z independently represent O, S, NH, or $NR^9$ where $R^9$ is alkyl or substituted alkyl.

In one particular embodiment, there are provided compounds of Formula IIa or its tautomer and/or a pharmaceutically acceptable salt thereof:

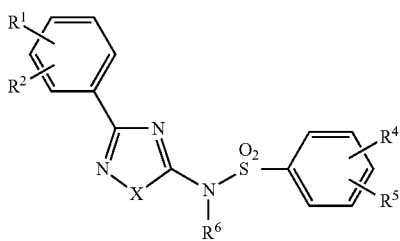

IIa wherein X is S or $NR^9$ where $R^9$ is alkyl or substituted alkyl; and $R^1$, $R^2$, $R^4$, $R^5$, and $R^6$ are as defined herein.

In one preferred embodiment, X is S. In another preferred embodiment, X is $NCH_3$.

In one preferred embodiment, $R^1$ and $R^2$ independently are selected from the group consisting of hydrogen, nitro, trifluoromethyl, cyano, and halo.

In one preferred embodiment, $R^4$ and $R^5$ independently are selected from the group consisting of hydrogen, alkyl, substituted alkyl, alkoxy, and substituted alkoxy.

In one preferred embodiment, $R^6$ is hydrogen.

In one preferred embodiment, there are provided compounds of Formula IIa wherein
X is S;
$R^1$ and $R^2$ independently are selected from the group consisting of hydrogen, nitro, trifluoromethyl, cyano, and halo;
$R^4$ and $R^5$ independently are selected from the group consisting of hydrogen, alkyl, substituted alkyl, alkoxy, and substituted alkoxy; and
$R^6$ is hydrogen; or
its tautomer and/or a pharmaceutically acceptable salt thereof.

In one particularly preferred embodiment, there are provided compounds of Formula IIa wherein
X is S;
$R^1$ and $R^2$ independently are hydrogen or nitro;
$R^4$ and $R^5$ independently are hydrogen, methyl, or methoxy; and
$R^6$ is hydrogen; or
its tautomer and/or a pharmaceutically acceptable salt thereof.

In one preferred embodiment, there are provided compounds of Formula IIa wherein
X is $NCH_3$;
$R^1$ and $R^2$ independently are selected from the group consisting of hydrogen, nitro, trifluoromethyl, cyano, and halo;
$R^4$ and $R^5$ independently are selected from the group consisting of hydrogen, alkyl, substituted alkyl, alkoxy, and substituted alkoxy; and
$R^6$ is hydrogen; or
its tautomer and/or a pharmaceutically acceptable salt thereof.

In one particularly preferred embodiment, there are provided compounds of Formula IIa wherein
X is $NCH_3$;
$R^1$ and $R^2$ independently are hydrogen;
$R^4$ and $R^5$ independently are hydrogen, methyl, or methoxy; and
$R^6$ is hydrogen; or
its tautomer and/or a pharmaceutically acceptable salt thereof.

In some embodiments, there are provided compounds selected from the group consisting of
3,4-dimethoxy-N-[3-phenyl-1,2,4-thiadiazol-5-yl]benzenesulfonamide;
4-methyl-N-[3-phenyl-1,2,4-thiadiazol-5-yl]benzenesulfonamide;
3,4-dimethoxy-N-[3-(3-nitrophenyl)-1,2,4-thiadiazol-5-yl]benzenesulfonamide;
4-methyl-N-[3-(3-nitrophenyl)-1,2,4-thiadiazol-5-yl]benzenesulfonamide;
3,4-dimethoxy-N-(1-methyl-3-phenyl-1,2,4-triazol-5-yl)benzenesulfonamide; and
4-methyl-N-(1-methyl-3-phenyl-1,2,4-triazol-5-yl)benzenesulfonamide.

In a particular embodiment, there are provided compounds of Formula IIb or its tautomer and/or a pharmaceutically acceptable salt thereof:

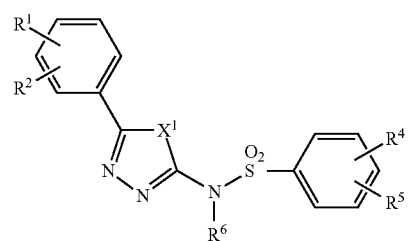

IIb wherein $X^1$ is S or NH; and $R^1$, $R^2$, $R^4$, $R^5$, and $R^6$ are as defined herein.

In one preferred embodiment, $X^1$ is S. In another preferred embodiment, $X^1$ is NH.

In one preferred embodiment, $R^1$ and $R^2$ independently are selected from the group consisting of hydrogen, nitro, trifluromethyl, cyano, and halo.

In one preferred embodiment, $R^4$ and $R^5$ independently are selected from the group consisting of hydrogen, alkyl, substituted alkyl, alkoxy, and substituted alkoxy.

In one preferred embodiment, $R^6$ is hydrogen.

In one preferred embodiment, there are provided compounds of Formula IIb wherein
$X^1$ is S;
$R^1$ and $R^2$ independently are selected from the group consisting of hydrogen, nitro, trifluromethyl, cyano, and halo;
$R^4$ and $R^5$ independently are selected from the group consisting of hydrogen, alkyl, substituted alkyl, alkoxy, and substituted alkoxy; and
$R^6$ is hydrogen; or
its tautomer and/or a pharmaceutically acceptable salt thereof.

In one particularly preferred embodiment, there are provided compounds of Formula IIb wherein
$X^1$ is S;
$R^1$ and $R^2$ independently are hydrogen or nitro;
$R^4$ and $R^5$ independently are selected from the group consisting of hydrogen, methyl, and methoxy; and R⁶ is hydrogen; or
its tautomer and/or a pharmaceutically acceptable salt thereof.

In one preferred embodiment, there are provided compounds of Formula IIb wherein
X¹ is NH;
R¹ and R² independently are hydrogen, nitro, trifluromethyl, cyano, or halo;
R⁴ and R⁵ independently are selected from the group consisting of hydrogen, alkyl, substituted alkyl, alkoxy, and substituted alkoxy; and
R⁶ is hydrogen; or
its tautomer and/or a pharmaceutically acceptable salt thereof.

In one particularly preferred embodiment, there are provided compounds of Formula IIb wherein
X¹ is NH;
R¹, R², and R⁶ independently are hydrogen; and
R⁴ and R⁵ independently are selected from the group consisting of hydrogen, methyl, and methoxy; or
its tautomer and/or a pharmaceutically acceptable salt thereof.

In some embodiments, there are provided compounds selected from the group consisting of
3,4-dimethoxy-N-[3-(phenyl)-1,2,4-triazol-5-yl]benzenesulfonamide;
4-methyl-N-[3-(phenyl)-1,2,4-triazol-5-yl]benzenesulfonamide;
3,4-dimethoxy-N-[3-(3-nitrophenyl)-1,2,4-triazol-5-yl]benzenesulfonamide;
4-methyl-N-[3-(3-nitrophenyl)-1,2,4-triazol-5-yl]benzenesulfonamide;
3,4-dimethoxy-N-[5-(phenyl)-1,3,4-thiadiazol-2-yl]benzenesulfonamide;
4-methyl-N-[5-(phenyl)-1,3,4-thiadiazol-2-yl]benzenesulfonamide;
3,4-dimethoxy-N-[5-(3-nitrophenyl)-1,3,4-thiadiazol-2-yl]benzenesulfonamide; and
4-methyl-N-[5-(3-nitrophenyl)-1,3,4-thiadiazol-2-yl]benzenesulfonamide.

In a particular embodiment, there are provided compounds of Formula IIc or their tautomers and/or a pharmaceutically acceptable salt thereof:

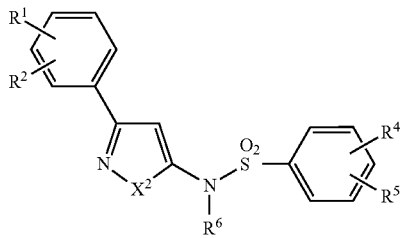

IIc wherein X² is O or NR⁹ where R⁹ is alkyl or substituted alkyl; and R¹, R², R³, R⁴, R⁵, and R⁶ are as defined herein.

In one preferred embodiment, X² is O. In another preferred embodiment, X² is NCH₃.

In one preferred embodiment, R¹ and R² independently are selected from the group consisting of hydrogen, nitro, trifluromethyl, cyano, or halo.

In one preferred embodiment, R⁴ and R⁵ independently are selected from the group consisting of hydrogen, alkyl, substituted alkyl, alkoxy, and substituted alkoxy.

In one preferred embodiment, R⁶ is hydrogen.

In one preferred embodiment, there are provided compounds of Formula IIc wherein
X² is O;
R¹ and R² independently are hydrogen, nitro, trifluromethyl, cyano, or halo;
R⁴ and R⁵ independently are selected from the group consisting of hydrogen, alkyl, substituted alkyl, alkoxy, and substituted alkoxy; and
R⁶ is hydrogen; or
its tautomer and/or a pharmaceutically acceptable salt thereof.

In one particularly preferred embodiment, there are provided compounds of Formula IIc wherein
X² is O;
R¹ and R² independently are hydrogen;
R⁴ and R⁵ independently are selected from the group consisting of hydrogen, methyl, and methoxy; and
R⁶ is hydrogen; or
its tautomer and/or a pharmaceutically acceptable salt thereof.

In one preferred embodiment, there are provided compounds of Formula IIc wherein
X² is NCH₃;
R¹ and R² independently are hydrogen;
R⁴ and R⁵ independently are selected from the group consisting of hydrogen, alkyl, substituted alkyl, alkoxy, and substituted alkoxy; and
R⁶ is hydrogen; or
its tautomer and/or a pharmaceutically acceptable salt thereof.

In one particularly preferred embodiment, there are provided compounds of Formula IIc wherein
X² is NCH₃;
R¹, R², and R⁶ independently are hydrogen;
R⁴ and R⁵ independently are selected from the group consisting of hydrogen, methyl, and methoxy; or
its tautomer and/or a pharmaceutically acceptable salt thereof.

In one embodiment, there are provided compounds selected from the group consisting of
3,4-dimethoxy-N-[3-(phenyl)-isoxazol-5-yl]benzenesulfonamide;
4-methyl-N-[3-(phenyl)-isoxazol-5-yl]benzenesulfonamide;
3,4-dimethoxy-N-[1-methyl-3-phenyl-pyrazol-5-yl]benzenesulfonamide; and
4-methyl-N-[1-methyl-3-phenyl-pyrazol-5-yl]benzenesulfonamide.

In another particular embodiment, there are provided compounds of Formula IId or its tautomer and/or a pharmaceutically acceptable salt thereof:

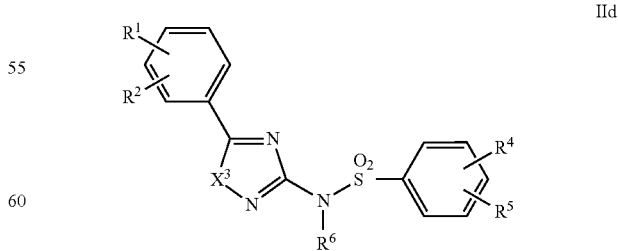

IId wherein X³ is S or NR⁹ where R⁹ is alkyl or substituted alkyl; and R¹, R², R⁴, R⁵, and R⁶ are as defined herein.

In one preferred embodiment, X³ is S. In another preferred embodiment, X³ is NCH₃.

In one preferred embodiment, $R^1$ and $R^2$ independently are selected from the group consisting of hydrogen, nitro, trifluoromethyl, cyano, and halo.

In one preferred embodiment, $R^4$ and $R^5$ independently are selected from the group consisting of hydrogen, alkyl, substituted alkyl, alkoxy, and substituted alkoxy.

In one preferred embodiment, $R^6$ is hydrogen.

In one preferred embodiment, there are provided compounds of Formula IId wherein
$X^3$ is S;
$R^1$ and $R^2$ independently are selected from the group consisting of hydrogen, nitro, trifluoromethyl, cyano, and halo;
$R^4$ and $R^5$ independently are selected from the group consisting of hydrogen, alkyl, substituted alkyl, alkoxy, and substituted alkoxy; and
$R^6$ is hydrogen; or
its tautomer and/or a pharmaceutically acceptable salt thereof.

In one particularly preferred embodiment, there are provided compounds of Formula IId wherein
$X^3$ is S;
$R^1$ and $R^2$ independently are hydrogen, nitro or chloro;
$R^4$ and $R^5$ independently are selected from the group consisting of hydrogen and methoxy; and
$R^6$ is hydrogen; or
its tautomer and/or a pharmaceutically acceptable salt thereof.

In some embodiments, there are provided compounds selected from the group consisting of
3,4-dimethoxy-N-[5-(4-chlorophenyl)-1,2,4-thiadiazole-3-yl]benzenesulfonamide;
3,4-dimethoxy-N-[5-(3-nitrophenyl)-1,2,4-thiadiazole-3-yl]benzenesulfonamide; and
3,4-dimethoxy-N-[5-(phenyl)-1,2,4-thiadiazole-3-yl]benzenesulfonamide.

In some embodiments, the compounds of the present invention are represented by general Formula III:

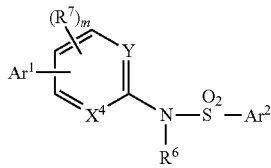

III $X^4$ and Y are independently selected from the group consisting of N and C—$R^8$;
$Ar^1$ and $Ar^2$ are independently selected from the group consisting of aryl, substituted aryl, heteroaryl, and substituted heteroaryl;
$R^6$ is selected from the group consisting of hydrogen, alkyl, substituted alkyl, aryl, substituted aryl, heteroaryl, and substituted heteroaryl;
$R^7$ is selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or 2 or more $R^7$ join to form a ring when m>1 where the ring is selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;
m is an integer from 0 to 3; and
$R^8$ is selected from the group consisting of hydrogen, alkyl, substituted alkyl, halo, amino, substituted amino, aryl, substituted aryl, heteroaryl, and substituted heteroaryl;
or its tautomer and/or a pharmaceutically acceptable salt thereof.

In one group of preferred embodiments, the compounds of the present invention are represented by Formulas IIIa through IIId:

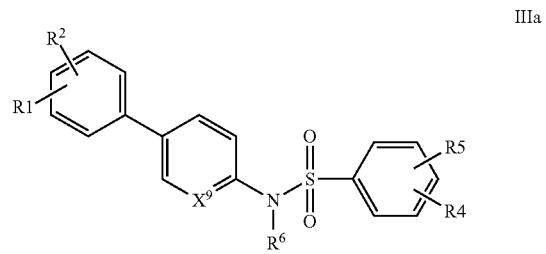

IIIa

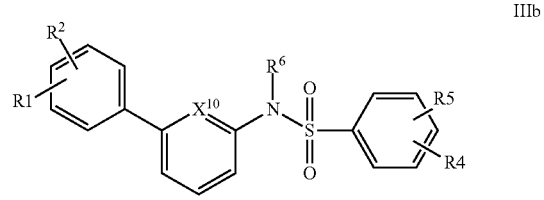

IIIb

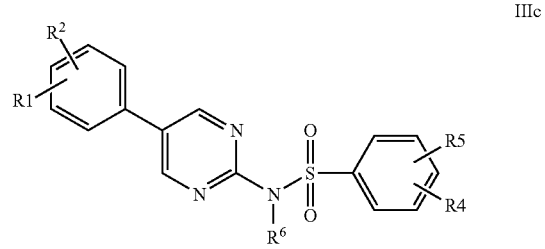

IIIc

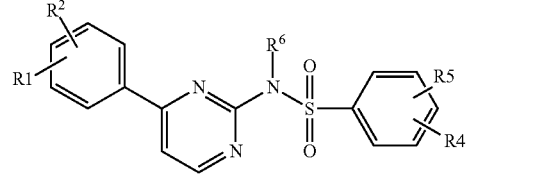

IIId

In Formulas IIIc through IIId, $R^1$, $R^2$, $R^4$, $R^5$, and $R^6$ are independently hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring, and/or $R^4$ and $R^5$ join together to form a ring where the ring is selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;
In Formulas IIIa and IIIb, $X^9$ and $X^{10}$ independently are N or CH.

Some preferred embodiments of the compounds of Formula III are as following. In some preferred embodiments, $X^4$ and Y independently are nitrogen. In some preferred embodiments, $X^4$ is nitrogen and Y is CH. In some preferred embodiments, $X^4$ and Y independently are CH.

In some preferred embodiments of the compounds of Formula III, $Ar^1$ and $Ar^2$ independently are aryl or substituted aryl. In some particularly preferred embodiments, $Ar^1$ is substituted aryl where the substitution is hydrogen, alkyl, or alkoxy. In some particularly preferred embodiments, $Ar^2$ is substituted aryl where the substitution is hydrogen, alkyl, or alkoxy.

In some preferred embodiments of the compounds of Formula III, $R^6$ is hydrogen. In some preferred embodiments, $R^7$ is hydrogen. In some preferred embodiments, $R^8$ is hydrogen.

In some embodiments, there are provided compounds selected from the group consisting of
potassium 3,4-dimethoxy-N-[biphenyl-3-yl]benzenesulfonamide;
3,4-dimethoxy-N-[5-(4-methoxyphenyl)-pyrimidin-2-yl]benzenesulfonamide;
4-methyl-N-[5-(4-methoxyphenyl)-pyrimidin-2-yl]benzenesulfonamide;
3,4-dimethoxy-N-[5-(phenyl)-pyridin-2-yl]benzenesulfonamide;
4-methyl-N-[5-(phenyl)-pyridin-2-yl]benzenesulfonamide; and
3,4-dimethoxy-N-[(1,1'-biphenyl)-4-yl]benzenesulfonamide.

The following Table 1 provides exemplary compounds according to some embodiments of the present invention.

TABLE 1

| Compound Structure | Compound Name |
| --- | --- |
| A1 | 3,4-dimethoxy-N-[3-(phenyl)-1,2,4-thiadiazol-5-yl]benzenesulfonamide |
| A2 | 4-methyl-N-[3-(phenyl)-1,2,4-thiadiazol-5-yl]benzenesulfonamide |
| A3 | 3,4-dimethoxy-N-[3-(3-nitrophenyl)-1,2,4-thiadiazole-5-yl]benzenesulfonamide |
| A4 | 4-methyl-N-[3-(3-nitrophenyl)-1,2,4-thiadiazole-5-yl]benzenesulfonamide |
| A5 | 3,4-dimethoxy-N-[5-(phenyl)-1,3,4-thiadiazol-2-yl]benzenesulfonamide |
| A6 | 4-methyl-N-[5-(phenyl)-1,3,4-thiadiazol-2-yl]benzenesulfonamide |

TABLE 1-continued

| Compound Structure | Compound Name |
|---|---|
| 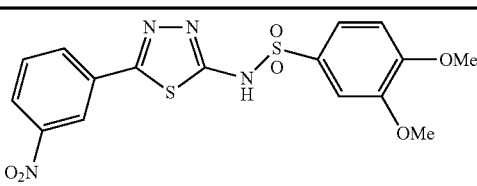<br>A7 | 3,4-dimethoxy-N-[5-(3-nitrophenyl)-1,3,4-thiadiazole-2-yl]benzenesulfonamide |
| 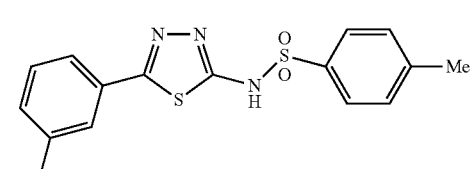<br>A8 | 4-methyl-N-[5-(3-nitrophenyl)-1,3,4-thiadiazole-2-yl]benzenesulfonamide |
| 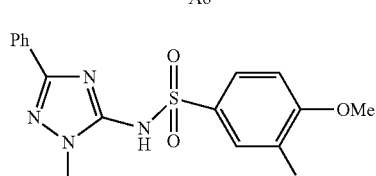<br>A9 | 3,4-dimethoxy-N-[3-(phenyl)-1,2,4-triazole-5-yl]benzenesulfonamide |
| 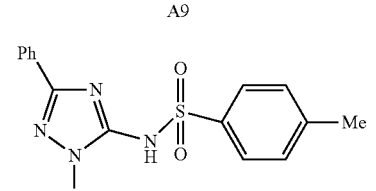<br>A10 | 4-methyl-N-[3-(phenyl)-1,2,4-triazole-5-yl]benzenesulfonamide |
| 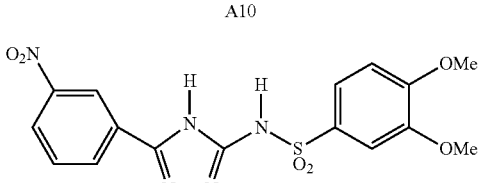<br>A11 | 3,4-Dimethoxy-N-[5-(3-nitrophenyl)-1,2,4-triazol-3-yl]benzenesulfonamide |
| 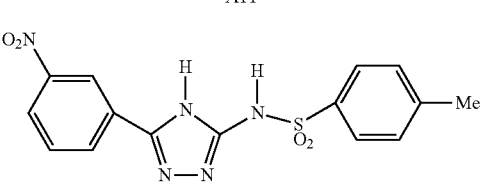<br>A12 | 4-Methyl-N-[5-(3-nitrophenyl)-1,2,4-triazol-3-yl]benzenesulfonamide |
| 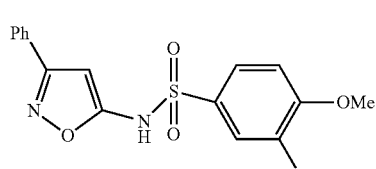<br>A13 | 3,4-dimethoxy-N-[3-(phenyl)-isoxazol-5-yl]benzenesulfonamide |
| 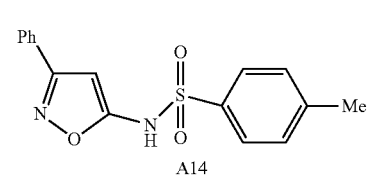<br>A14 | 4-methyl-N-[3-(phenyl)-isoxazol-5-yl]benzenesulfonamide |

TABLE 1-continued

| Compound Structure | Compound Name |
| --- | --- |
| A15 | 3,4-dimethoxy-N-[1-methyl-3-phenyl-pyrazole-5-yl]benzenesulfonamide |
| A16 | 4-methyl-N-[1-methyl-3-phenyl-pyrazole-5-yl]benzenesulfonamide |
| A17 | 3,4-dimethoxy-N-(1-methyl-3-phenyl-1,2,4-triazol-5-yl)benzenesulfonamide |
| A18 | 4-methyl-N-(1-methyl-3-phenyl-1,2,4-triazol-5-yl)benzenesulfonamide |
| A19 | 3,4-dimethoxy-N-[5-(4-chlorophenyl)-1,2,4-thiadiazole-3-yl]benzenesulfonamide |
| A20 | 3,4-dimethoxy-N-[5-(3-nitrophenyl)-1,2,4-thiadiazole-3-yl]benzenesulfonamide |
| A21 | 3,4-dimethoxy-N-[5-(phenyl)-1,2,4-thiadiazole-3-yl]benzenesulfonamide |

TABLE 1-continued

| Compound Structure | Compound Name |
|---|---|
| 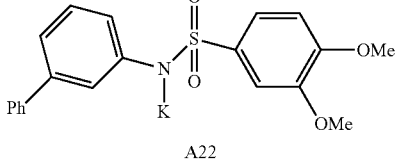 A22 | Potassium 3,4-dimethoxy-N-[biphenyl-3-yl]benzenesulfonamide |
| 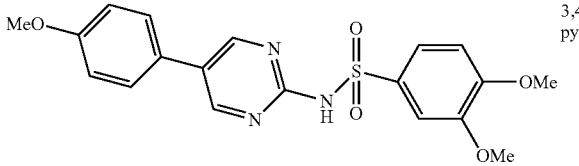 A23 | 3,4-dimethoxy-N-[5-(4-methoxyphenyl)-pyrimidine-2-yl]benzenesulfonamide |
| 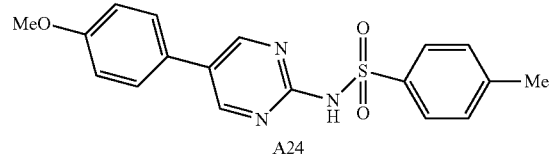 A24 | 4-methyl-N-[5-(4-methoxyphenyl)-pyrimidine-2-yl]benzenesulfonamide |
| 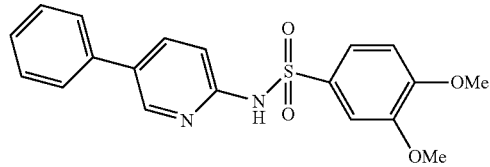 A25 | 3,4-dimethoxy-N-[5-(phenyl)-pyridine-2-yl]benzenesulfonamide |
| 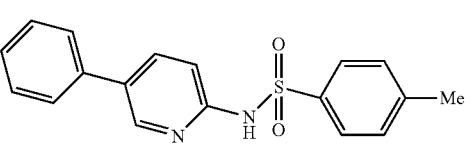 A26 | 4-methyl-N-[5-(phenyl)-pyridine-2-yl]benzenesulfonamide |
| 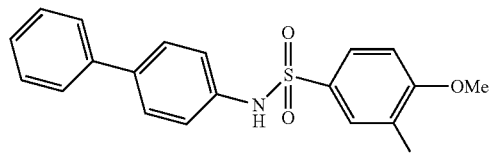 A27 | 3,4-dimethoxy-N-[biphenyl-4-yl]benzenesulfonamide |

3. COMPOSITIONS AND METHODS OF THE INVENTION

This invention provides compounds and composition which are useful in therapeutic applications. In particular, the compounds represented by Formula I, II, IIa, IIb, IIc, IId, IIe, IIf, IIg, III, IIIa, IIIb, IIIc, or IIId and their salts and/or tautomers can effectively act as inhibitors of kynurenine-3-monooxygenase (KMO) and inhibit the KMO activities in the brain. In one aspect of the invention, the invention provides pharmaceutical compositions comprising one or more compounds of Formula I, II, IIa, IIb, IIc, IId, IIe, IIf, IIg, III, IIIa, IIIb, IIIc, or IIId and a pharmaceutically acceptable excipient.

In one of its method aspects, this invention is directed to a method for inhibiting activity of kynurenine-3-monooxygenase activity which method comprises contacting cells (including neurons/microglia/invading macrophages) with an effective amount of one or more compounds of Formula I, II, IIa, IIb, IIc, IId, IIe, IIf, IIg, III, IIIa, IIIb, IIIc, or IIId. The compounds of the invention are useful in inhibiting the activity of kynurenine-3-monooxygenase activity in the CNS as well as in peripheral immune cells. The compounds are also useful for treating peripheral infections or immune dysfunction.

In another of its method aspects, this invention is directed to a method for treating a disease mediated at least in part by kynurenine-3-monooxygenase which method comprises administering to a patient an effective amount of one or more compounds of Formula I or a pharmaceutical composition comprising a pharmaceutically acceptable excipient and one or more compounds of Formula I, II, IIa, IIb, IIc, IId, IIe, IIf, IIg, III, IIIa, IIIb, IIIc, or IIId.

Diseases mediated at least in part by kynurenine-3-monooxygenase include those selected from the group consisting of Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behaviour, schizophrenia, chronic anxiety, depressive disorders, disorders of the developing or aged brain, diseases of addiction, diabetes, and complications thereof. The compounds of this invention may also influence synaptogenesis after brain injury. The compounds also may influence memory. The diseases of addiction refer to addictive diseases which adversely affect or alter the neuronal function including by way of example, drug addiction such as alcoholism, nicotine addiction, illicit drug addiction (e.g., heroine, cocaine, marijuana, etc.).

The compounds are useful in the diagnosis and treatment of a variety of human diseases including neurodegenerative and neurological disorders, consequences of stroke and/or cerebral ischaemia, hypoxia, multi-infarct dementia, consequences of trauma and damages to the cerebrum or spinal cord, autoimmune disease, and psychiatric illness. For example, the compounds of the present invention are particularly useful in treating neurodegenerative disorders such as Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behaviour, schizophrenia, chronic anxiety, depressive disorders, disorders of the developing or aged brain, diseases of addiction, diabetes, and complications thereof. The compounds of this invention may also influence synaptogenesis after brain injury. The compounds also may influence memory.

4. GENERAL SYNTHETIC METHODS

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Synthesis of Compounds of the Invention

In one general embodiment, the method involves reacting an appropriate benzenesulfonyl halide with an appropriate amine.

For example, the compounds of general Formula I can be prepared according to Scheme 1:

Scheme 1

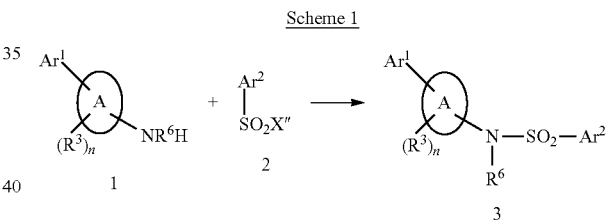

wherein X" represents halogen and R³, R⁶, A, Ar¹, Ar², and integer n are as defined herein.

In Scheme 1, compound 1 is combined with an equimolar amount and preferably an excess of compound 2 under coupling conditions to provide for compound 3. Specifically, this reaction is typically conducted by reacting amino compound 1 with at least one equivalent, preferably about 1.1 to about 2 equivalents, of sulfonyl halide (e.g., chloride), compound 2, in an inert diluent such as dichloromethane and the like. Generally, the reaction is conducted at a temperature ranging from about −70° C. to about 40° C. for about 1 to about 24 h. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Alternatively, compound 1 can be reacted with compound 2 in pyridine solution where pyridine acts both as a base and as a solvent. Upon completion of the reaction, the resulting N-sulfonyl compound 3 is recovered by conventional methods including neutralization, extraction, precipitation, chromatography, filtration, and the like.

The sulfonyl halides of compound 2 are either known compounds or compounds that can be prepared from known compounds by conventional synthetic procedures. Such compounds are typically prepared from the corresponding sulfonic acid, i.e., from compounds of the formula $Ar^2SO_3H$ where $Ar^2$ is as defined herein, using phosphorus trihalide and phosphorus pentahalide. This reaction is generally conducted by contacting the sulfonic acid with about 2 to 5 molar equivalents of phosphorus trihalide and phosphorus pentahalide, either neat or in an inert solvent, such as dichloromethane, at temperature in the range of about 0° C. to about 80° C. for about 1 to about 48 h to afford the sulfonyl halide. Alternatively, the sulfonyl halides can be prepared from the corresponding thiol compound, i.e., from compounds of the formula $Ar^2$—SH where $Ar^2$ is as defined herein, by treating the thiol with chlorine ($Cl_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl compound 3.

Amino compound 1 is prepared from known compounds or can be prepared in analogy to known methods. For example, the appropriate aryl-substituted amino-thiazole can be prepared according to Scheme 2:

Scheme 2

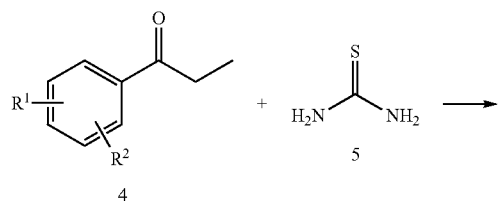

4    5

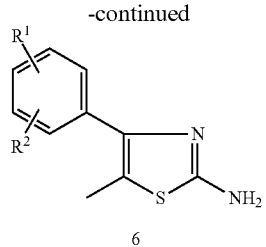

6 where $R^1$ and $R^2$ are as described herein.

This reaction is typically conducted by adding equimolar amounts of compound 4 and 5 in a polar solvent, such as ethanol or isopropanol, at a temperature ranging from about 40° C. to about 100° C. The product can be recovered by conventional methods such as crystallization.

Other known heterarylamines can be prepared in a manner similar to the above and are illustrated in the examples below. Alternatively, heteroarylamines can be prepared using methodology well known in the art such as Suzuki coupling of an aromatic or heteroaromatic halide with an aromatic or heteroaromatic boron derivative using techniques well known in the art. Typically some of such heteroarylamines can be commercially available from vendors such as Aldrich Chemical Company including, for example, 3-amino-5-phenylpyrazole, 2-amino-5-phenyl-1,3,4-thiadiazole, 2-amino-4-(p-tolyl)-thiazole, 2-amino-4-(4-bromophenyl)-thiazole, 2-amino-4-(4-chlorophenyl)-thiazole, and the like.

The compounds of the general Formula III can be prepared according to Scheme 3:

Scheme 3

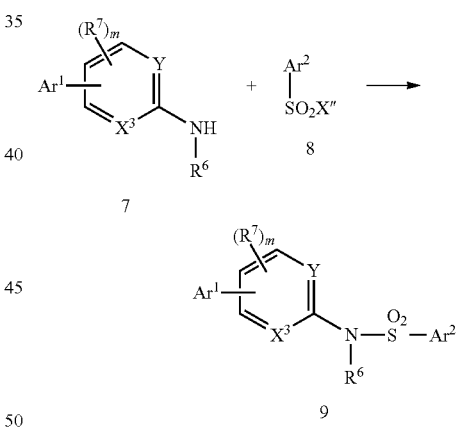

wherein X″ represents halogen and $X^3$, Y, $Ar^1$, $Ar^2$, $R^6$, $R^7$, and m are as defined herein.

Scheme 3 proceeds substantially as described above for Scheme 1.

Heteroarylamines or arylamines represented by compound 7 can be prepared in a manner similar to the above and are illustrated in the examples below. Alternatively, heteroarylamines and arylamines can be prepared using methodology well known in the art such as Suzuki coupling of an aromatic or heteroaromatic halide with an aromatic or heteroaromatic boron derivative using techniques well known in the art. Typically some of these 6 membered aryl and heteroarylamines can be commercially available from vendors such as Aldrich Chemical Company including, for example, 2-(2-aminophenyl)indole, 2-aminobiphenyl, 4-aminobiphenyl, and the like.

The compounds of the general Formula IIb such as 1,2,4-triazole compounds can be prepared according to Scheme 4:

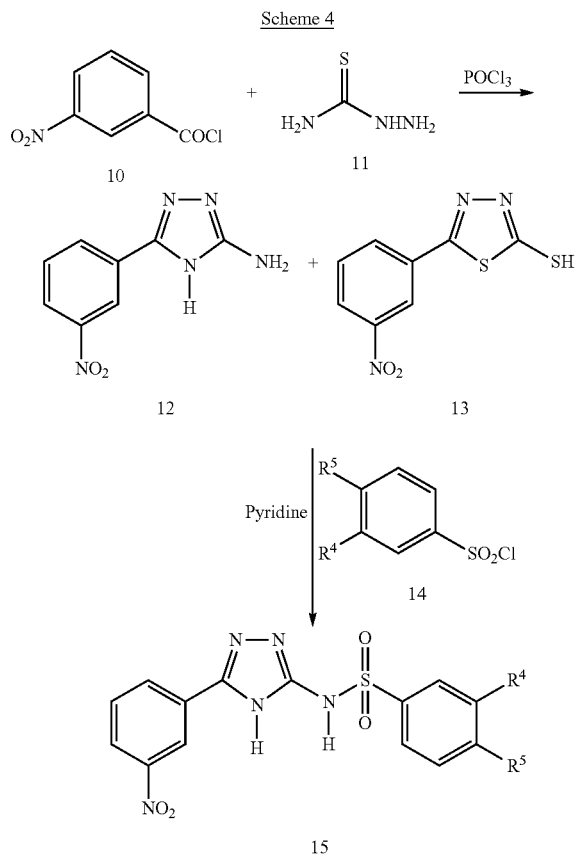

where R⁴ and R⁵ are as described herein.

This reaction is typically conducted by adding an equimolar amounts of 3-nitrobenzoyl chloride 10 and thiosemicarbazide 11 to phosphorus oxychloride and refluxing the reaction mixture. The product can be recovered by conventional methods such as filtration where the reaction results in a mixture of aminotriazole 12 and thiadiazole 13. The mixture can be used as such and is stirred at room temperature with 3,4-dimethoxybenzenesulfonyl chloride 14. The product can be recovered by conventional methods such as filtration and/or crystallization.

Such derivations are contemplated to allow for active metabolites to be formed in the brain rather than in the peripheral circulation and inhibits KMO activity in the brain upon metabolic activation as an irreversible enzyme inhibitor.

5. USE OF COMPOUNDS OF THE INVENTION

The compounds in accordance with the present invention have high activities as inhibitors of kynurenine-3-monooxygenase.

The KMO inhibiting activities of the compounds of the present invention were evaluated using standard methods. See Erickson et al., A Radiometric Assay for Kynurenine 3-Hydroxylase Based on the Release of $^3H_2O$ During Hydroxylation of L-[3,5-$^3$H]-Kynurenine, Anal. Biochem. 1992, 205, 257-262, the disclosure of which is hereby incorporated by reference.

Table 2 shows $IC_{50}$ values or percent inhibition for some of the compounds of this invention. The $IC_{50}$ value is the half maximal inhibitory concentration and represents the concentration of an inhibitor that is required for 50% inhibition of an enzyme activity and the percent inhibition measures the amount of enzyme activity inhibited at a given concentration of compound. If the administered compound is a prodrug then the prodrug may not inhibit KMO until it has metabolized appropriately.

TABLE 2

| Compound# | % inhibition at 10 uM |
|---|---|
| A1 | 73.61 |
| A2 | 77.9 |
| A5 | 60.03 |
| A6 | 71.59 |
| A13 | 17.82 |
| A14 | 30.74 |
| A15 | * |
| A16 | * |
| A9 | * |
| A10 | * |
| A19 | 68.6 |
| A22 | 19.57 |
| A23 | 17.5 |
| A24 | * |
| A25 | 24.8 |
| A26 | * |
| A27 | * |

The compounds in this table have been identified in Table 1 herein
*The compounds are contemplated to have inhibition activity at higher concentrations

6. ADMINISTRATION AND PHARMACEUTICAL COMPOSITION

The present invention provides novel compounds possessing KMO inhibition activity and, accordingly, are useful in treating disorders mediated by (or at least in part by) the presence of 3-hydroxykynurenine and/or quinolinic acid. Such diseases include, for example, Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behaviour, schizophrenia, chronic anxiety, depressive disorders, disorders of the developing or aged brain, diabetes, and complications thereof.

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, preferably once or twice a day.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, 18$^{th}$ ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

This invention is not limited to any particular composition or pharmaceutical carrier, as such may vary. In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present invention based on the total formulation, with the balance being one or more suitable pharmaceutical excipients. Preferably, the compound is present at a level of about 1-80 wt %. Representative pharmaceutical formulations are described below.

FORMULATION EXAMPLES

The following are representative pharmaceutical formulations containing a compound of formula I.

Formulation Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Formulation Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Formulation Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4

Injectable Formulation

The following ingredients are mixed to form an injectable formulation.

| Ingredient | Amount |
|---|---|
| compound of this invention | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Formulation Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
|---|---|
| Compound of the invention | 500 mg |
| Witepsol ® H-15 | balance |

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.
bd=broad doublet
bm=broad multiplet
bs=broad singlet
$CH_2Cl_2$=dichloromethane d=doublet
dd=doublet of doublets
DMF=dimethylformamide
DMSO=dimethyl sulfoxide
EtOAc=ethyl acetate
EtOH=ethanol
g=gram
h=hour/s
HCl=hydrochloric acid
HOAc=acetic acid
Hz=hertz
KOH=potassium hydroxide
m=multiplet
M=molar
MeOH=methanol
mg=milligrams
mL=milliliters
mmol=millimols
mp=melting point
MS=mass spectroscopy
m/z=mass to charge ratio
NMR=nuclear magnetic resonance
NaOH=sodium hydroxide
$Na_2SO_4$=sodium sulfate
s=singlet
t=triplet
TLC=thin layer chromatography
UV=ultraviolet
wt %=weight percent Example 1

3,4-Dimethoxy-N-[3-(phenyl)-1,2,4-thiadiazol-5-yl]benzenesulfonamide

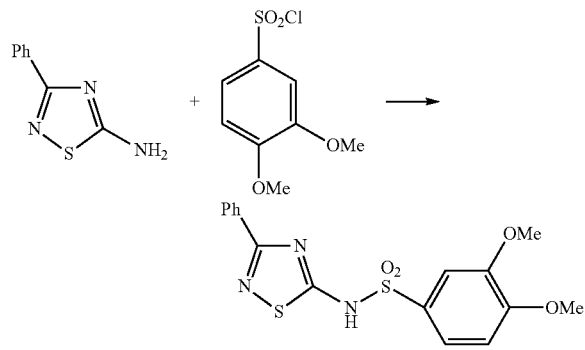

3-Phenyl-1,2,4-thiadiazol-5-amine (326 mg, 1.84 mmol) was dissolved in dry pyridine (10 mL). Then 3,4-dimethoxybenzenesulfonyl chloride (529 mg, 2.23 mmol) was added. The solution was stirred at room temperature under Argon. After 46 h, the pyridine was removed in vacuo and flashed off with toluene. The residue was partitioned between EtOAc and 1M NaOH. The organic phase was washed with 1M NaOH until no turbidity was observed on rectification of a small sample. The alkaline phase was made acidic (~pH 3) with 1M HCl and extracted with EtOAc. After drying over $Na_2SO_4$, the solvent was removed in vacuo to give a solid (100 mg) which was crystallized from EtOAc. Yield was 29.3 mg; mp 170-171° C.

$^1$H NMR (DMSO $d_6$) δ 3.80 (s, 3H), 3.81 (s, 3H), 7.11 (d, J=8.4 Hz, 1H), 7.30 (d, J=2.0 Hz, 1H), 7.46 (dd, J=2.0, 8.4 Hz, 1H), 7.49-7.57 (m, 3H), 7.98 (m, 2H).

Example 2

4-Methyl-N-[3-(phenyl)-1,2,4-thiadiazol-5-yl]benzenesulfonamide

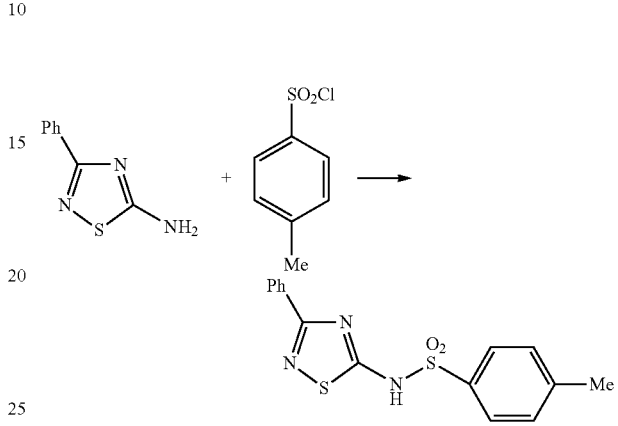

3-Phenyl-1,2,4-thiadiazol-5-amine or 3-phenyl-5-amino-1,2,4-thiadiazole (326 mg, 1.84 mmol) was dissolved in dry pyridine (10 mL) and 4-methylbenzenesulfonyl chloride (427 mg) was added and the solution was stirred at room temperature for 48 h. Using the same procedure as Example 3 except that the initial partition was between 1 M NaOH and $CH_2Cl_2$. The pyridine was removed in vacuo and flashed off with toluene. The residue was partitioned between $CH_2Cl_2$ and 1M NaOH. The organic phase was washed with 1 M NaOH until no turbidity was observed on rectification of a small sample. The alkaline phase was made acidic (~pH 3) with 1M HCl and extracted with EtOAc. After drying over $Na_2SO_4$, the solvent was removed in vacuo. The crude product was crystallized from EtOH. A first crop of white needles 57.4 g was obtained, mp 217-218° C. A second crop (18.3 mg) of slightly pink product was obtained from 70% ethanol, mp 215-216° C.

$^1$H NMR (DMSO $d_6$) δ 2.36 (s, 3H), 7.38 (d, J=8.2 Hz, 2H), 7.50-7.57 (m, 3H), 7.75 (d, J=8.2 Hz, 2H), 7.98 (bd, 2H).

Example 3

Potassium 3,4-dimethoxy-N-[biphenyl-3-yl]benzenesulfonamide

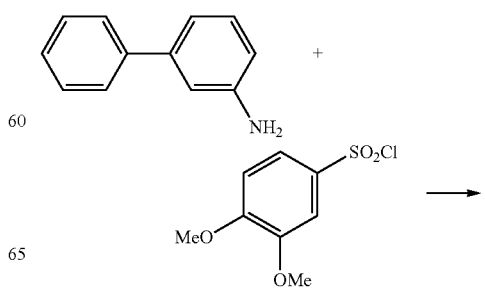

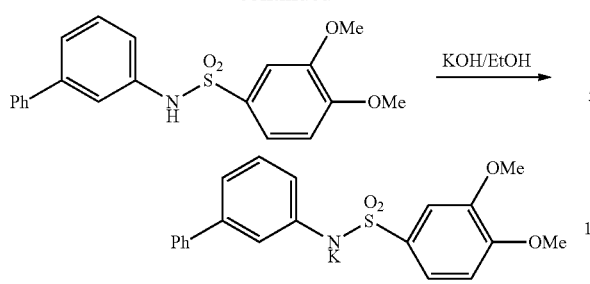

To a solution of biphenyl-3-amine (338 mg, 2 mmol) in dry pyridine (10 mL) was added 3,4-dimethoxybenzenesulfonyl chloride (529 mg, 2.23 mmol). The mixture was left at room temperature for 69 h. After the pyridine was removed in vacuo, the residue was partitioned between $CH_2Cl_2$ and NaOH. A very viscous oil (0.664 g, 1.8 mmol) was obtained and then dissolved in 10 mL of EtOH and a solution of KOH in EtOH (7.3 mL of a solution containing 322 mg of 85% KOH in 20 mL of EtOH). The solvent was removed in vacuo leaving a viscous oil. This was taken up in EtOH and diluted with an equal amount of toluene. A solid crystallized on standing. It was collected by filtration, washed with toluene and dried in vacuo to give 600 mg of a white solid, mp 262-264° C.

Example 4

3,4-Dimethoxy-N-[3-(phenyl)-1,2,4-triazol-5-yl]benzenesulfonamide

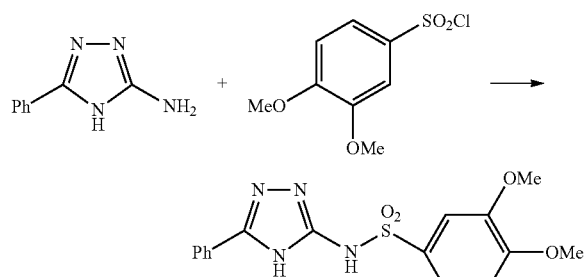

To a solution of 5-phenyl-4H-1,2,4-triazol-3-amine (354 mg, 2 mmol) in dry pyridine (10 mL) was added 3,4-dimethoxybenzenesulfonyl chloride (529 mg, 2.23 mmol). The solution was stirred at room temperature under Argon. After 48 h, the pyridine was removed in vacuo and flashed off with toluene. The residue was partitioned between $CH_2Cl_2$ and 1M NaOH. The organic phase was washed with 1M NaOH until no turbidity was observed on rectification of a small sample. The alkaline phase was made acidic (~pH 3) with 1M HCl and extracted with $CH_2Cl_2$. After drying over $Na_2SO_4$, the solvent was removed in vacuo to give 0.47 g crude product. The crude product was dissolved in hot HOAc (22 mL), diluted with water (9 mL) and seeded. The product was collected by filtration, washed with water, then EtOH and dried in vacuo to give 361 mg of a granular white solid, mp 245-246° C.

$^1$H NMR (DMSO $d_6$) δ 3.79 (s, 6H), 7.08 (bm, 1H), 7.43-7.48 (bm, 6H), 7.84 (bs, 2H), 10.91 (bs, 1H).

Example 5

4-Methyl-N-[3-(phenyl)-1,2,4-triazol-5-yl]benzenesulfonamide

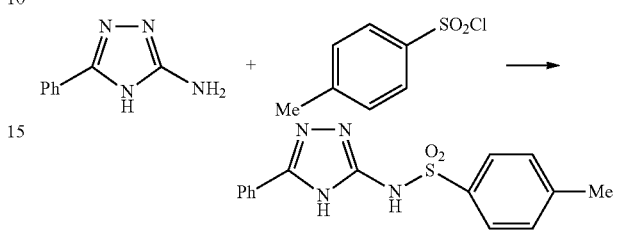

To a solution of 5-phenyl-4H-1,2,4-triazol-3-amine (354 mg, 2 mmol) in dry pyridine (10 mL) was added 4-methylbenzenesulfonyl chloride (427 mg, 2.24 mmol). The solution was stirred at room temperature under Argon. After 48 h, the pyridine was removed in vacuo and flashed off with toluene. The residue was partitioned between $CH_2Cl_2$ and 1M NaOH. The organic phase was washed with 1M NaOH until no turbidity was observed on rectification of a small sample. The alkaline phase was made acidic (~pH 3) with 1M HCl and extracted with $CH_2Cl_2$. After drying over $Na_2SO_4$, the solvent was removed in vacuo to give 0.41 g crude product. The crude product was dissolved hot EtOAc (16 mL), diluted with hexane (16 mL), and seeded to give fine white needles (304 mg) with mp 220-221° C.

$^1$H NMR (DMSO $d_6$) δ 2.34 (s, 3H), 7.31-7.36 (bm, 3H), 7.48 (bs, 3H), 7.77-7.84 (bm, 4H), 11.04 (bs, 1H).

Example 6

3,4-Dimethoxy-N-[3-(phenyl)-isoxazol-5-yl]benzenesulfonamide

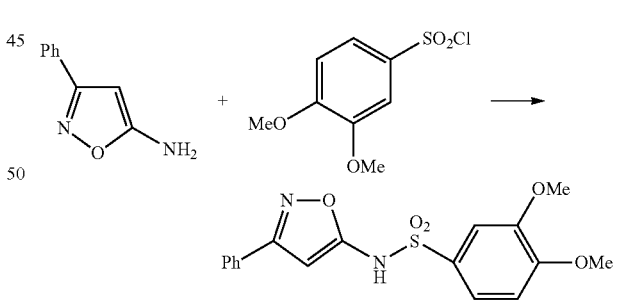

To a solution of 3-phenylisoxazol-5-amine (320 mg, 2 mmol) in 10 mL of dry pyridine was added 3,4-dimethoxybenzenesulfonyl chloride (529 mg, 2.23 mmol). The solution was stirred at room temperature under Argon. After 24 h, the pyridine was removed in vacuo and flashed off with toluene. The residue was partitioned between $CH_2Cl_2$ and 1M NaOH. The organic phase was washed with 1M NaOH until no turbidity was observed on rectification of a small sample. The alkaline phase was made acidic (~pH 3) with 1M HCl and extracted with $CH_2Cl_2$. After drying over $Na_2SO_4$, the solvent was removed in vacuo. The crude product was crystallized

Example 7

4-Methyl-N-[3-(phenyl)-isoxazol-5-yl]benzenesulfonamide

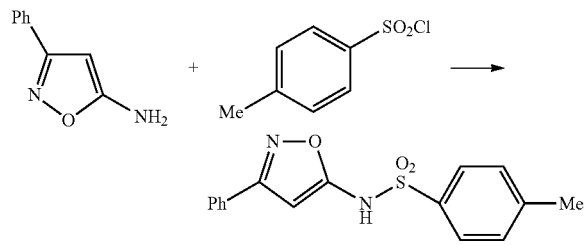

To a solution of 3-phenylisoxazol-5-amine (320 mg) in 10 mL of dry pyridine was added 4-methylbenzenesulfonyl chloride (427 mg, 2240 mmol). The solution was stirred at room temperature under Argon. After 25 h, the pyridine was removed in vacuo and flashed off with toluene. The residue was partitioned between $CH_2Cl_2$ and water. The $CH_2Cl_2$ phase was dried over $Na_2SO_4$ and the solvent was removed in vacuo. The oily residue partially crystallized on titration with EtOH. The product was crystallized from EtOH to give 61 mg of pink needles. The product was a single spot by TLC (1% MeOH in $CH_2Cl_2$, $SiO_2$, UV) less polar than starting material with mp 191-193° C.

Example 8

3,4-Dimethoxy-N-[5-(4-methoxyphenyl)-pyrimidine-2-yl]benzenesulfonamide

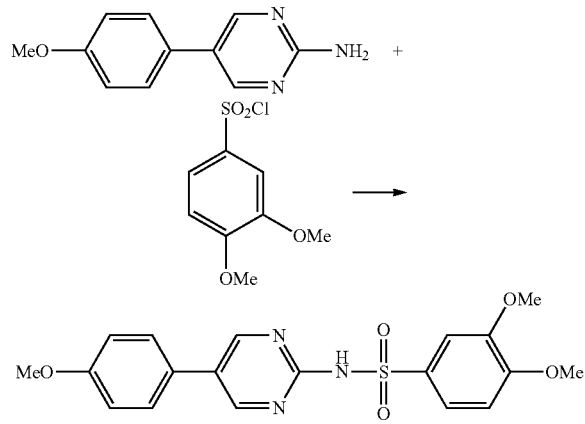

To a solution of 5-(4-methoxyphenyl)pyrimidin-2-amine (302 mg, 1.5 mmol) in 10 mL of dry pyridine was added 3,4-dimethoxybenzenesulfonyl chloride (398 mg, 1.68 mmol). The solution was stirred at room temperature under Argon. After 24 h, the pyridine was removed in vacuo and flashed off with toluene. The residue was partitioned between EtOAc and 1M HCl. EtOAc phase was washed with water to neutral, dried over $Na_2SO_4$ and evaporated in vacuo to give 0.20 g of a solid which was taken up in 4 mL of hot HOAc, diluted with 2 mL of water which initiated crystallization to give 181 mg of product with mp 218-220° C.

$^1$H NMR (DMSO $d_6$) δ 3.76-3.83 (m, 9H), 6.99-7.03 (m, 2H), 7.09-7.13 (m, 1H), 7.56-7.63 (m, 4H), 8.79, 8.80 (singlets, total 1H), 10.23 (s, 1H).

Example 9

4-Methyl-N-[5-(4-methoxyphenyl)-pyrimidine-2-yl]benzenesulfonamide

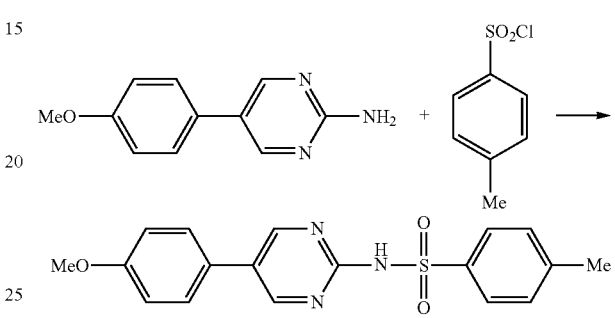

To a solution of 5-(4-methoxyphenyl)pyrimidin-2-amine (302 mg, 1.5 mmol) in 10 mL of dry pyridine was added 4-methylbenzenesulfonyl chloride (320 mg, 1.68 mmol). The solution was stirred at room temperature under Argon. After 21 h, the pyridine was removed in vacuo and flashed off with toluene. The residue was partitioned between $CH_2Cl_2$ and 1M NaOH. The organic phase was washed with 1M NaOH until no turbidity was observed on rectification of a small sample. The alkaline phase was made acidic (~pH 3) with 1M HCl and extracted with EtOAc. The crude solid product weighed 180 mg. The crude product was taken up in hot HOAc (4 mL) and diluted with 2 mL of water to initiate crystallization. The product was collected by filtration, washed with water and EtOH and dried in vacuo to give white needles (147 mg) with mp 220-223° C.

Example 10

3,4-Dimethoxy-N-[1-methyl-3-phenyl-pyrazol-5-yl]benzenesulfonamide

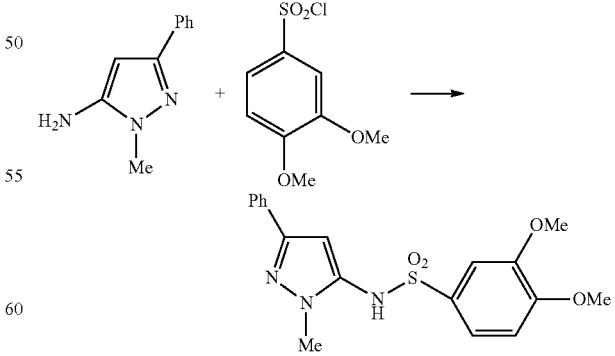

To a solution of 1-methyl-3-phenyl-pyrazol-5-amine (346 mg, 2 mmol) in 10 mL of dry pyridine was added 529 mg (2.23 mmol) of 3,4-dimethoxybenzenesulfonyl chloride. The solution was stirred at room temperature under Argon. After 22 h, the pyridine was removed in vacuo and flashed off with toluene. The crude base soluble material (1M NaOH) weighed 1.1 g. The crude product was taken up in EtOAc and extracted with 1M NaOH and H₂O alternately. The basic aqueous phase was made acidic with 1M HCl, extracted with EtOAc, washed with water, dried and evaporated in vacuo to give a cream colored solid (0.70 g) which was taken up in 5 mL of hot EtOH, diluted with 5 mL of H₂O and seeded to give 473 mg of a solid with mp 163-165° C. after drying in vacuo.

$^1$H NMR (DMSO d$_6$) δ 3.59 (s, 3H), 3.75 (s, 3H), 3.83 (s, 3H), 6.19 (s, 1H), 7.12 (d, J=8.4 Hz, 1H), 7.24-7.28 (m, 2H), 7.31-7.36 (m, 3H), 7.67 (d, J=7.2 Hz, 2H).

$^{13}$C NMR (DMSO d$_6$) δ 35.331, 55.705, 55.841, 98.365, 109.285, 111.168, 124.7, 127.555, 128.595, 130.744, 132.924, 135.938, 148.247, 152.507.

Example 11

4-Methyl-N-[1-methyl-3-phenyl-pyrazol-5-yl]benzenesulfonamide

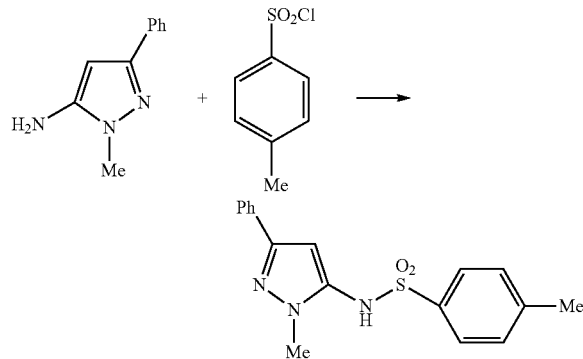

To a solution of 1-methyl-3-phenyl-pyrazol-5-amine (346 mg, 2 mmol) in dry pyridine was (10 mL) added 427 mg (2.24 mmol) of 4-methylbenzenesulfonyl chloride. The solution was stirred at room temperature under Argon. After 25 h, the pyridine was removed in vacuo and flashed off with toluene, and the residue was partitioned between EtOAc and 1M HCl. After washing with water and drying over Na₂SO₄, the solvent was removed in vacuo to give 0.67 g of a 1M NaOH soluble solid. The product was taken up in 15 mL of EtOAc, diluted with 15 mL of hexane and seeded to give 0.429 g of a yellow solid which was a single spot on TLC (SiO₂, UV, 5% MeOH in CH₂Cl₂) with mp 206-208° C.

$^1$H NMR (DMSO d$_6$) δ 2.37, 2.39 (singlets, total 3H), 3.57, 3.58 (singlets, total 3H), 6.15, 6.16 (singlets, total 1H), 7.23-7.42 (m, 7H), 7.64-7.66 (m, 2H), 10.38, 10.39 (singlets, total 1H).

Example 12

3,4-Dimethoxy-N-(1-methyl-3-phenyl-1,2,4-triazol-5-yl)benzenesulfonamide

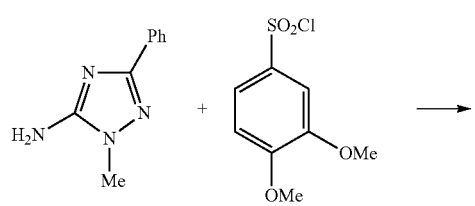

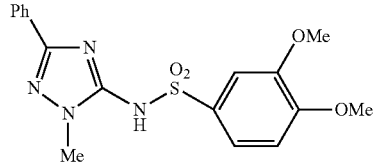

To a solution of 1-methyl-3-phenyl-1,2,4-triazol-5-amine (320 mg, 2 mmol) in 10 mL dry pyridine was added 529 mg (2.23 mmol) of 3,4-dimethoxybenzenesulfonyl chloride. The solution was stirred at room temperature under Argon. After 21 h, the pyridine was removed in vacuo and flashed off with toluene. The salt was partitioned between EtOAc and water. The EtOAc phase was extracted alternately with 1M NaOH and H₂O. The basic phase was made acid (pH~3) with 1M HCl and extracted with EtOAc. The organic phase was evaporated in vacuo, toluene was added and was again evaporated in vacuo to give a white solid. The product was taken up in hot HOAc (16 mL), diluted with H₂O (10 mL) and seeded to give 143 mg of white needles with mp 279-280° C. after drying in vacuo.

Example 13

4-Methyl-N-(1-methyl-3-phenyl-1,2,4-triazol-5-yl)benzenesulfonamide

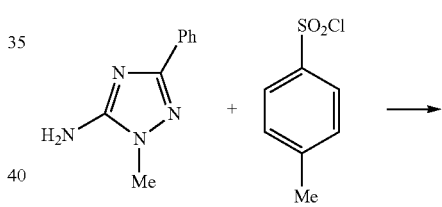

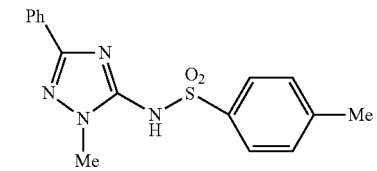

To a solution of 1-methyl-3-phenyl-1,2,4-triazol-5-amine (320 mg, 2 mmol) in 10 mL of dry pyridine was added 427 mg of 4-methylbenzenesulfonyl chloride (224 mmol). The solution was stirred at room temperature under Argon. After 23 h, the pyridine was removed in vacuo and flashed off with toluene, and the residue was partitioned between 1M NaOH and EtOAc. The alkaline phase was made acidic and the flocculent solid was collected by filtration and taken up in acetone. The aqueous phase was extracted with EtOAc, washed with H₂O and dried over Na₂SO₄. The acetone and the EtOAc phases were combined and evaporated in vacuo to give 0.15 g of a white solid which was taken up in hot HOAc (7 mL), diluted with water (4 mL), and seeded to give 80 mg of needles with mp 300-302° C.

Example 14

3,4-Dimethoxy-N-[5-(phenyl)-pyridine-2-yl]benzenesulfonamide

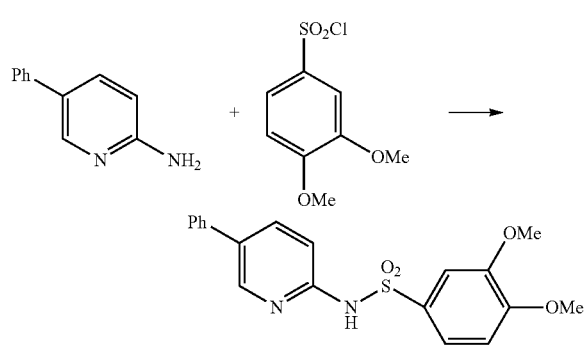

To a solution of 5-phenylpyridin-2-amine (340 mg, 2 mmol) in 10 mL of dry pyridine was added 3,4-dimethoxybenzenesulfonyl chloride (529 mg, 2.23 mmol). The solution was stirred at room temperature under Argon. After 19 h, the pyridine was removed in vacuo and flashed off with toluene, the solid residue was partitioned between EtOAc and 1M NaOH. The alkaline phase was made acidic and the solid was collected by filtration and dried in vacuo to give 511 mg of a solid. This was taken up in 5 mL of HOAc, diluted with 3 mL of water; crystallization took place to give 447 mg of a white crystalline product with mp 202-204° C.

$^1$H NMR (DMSO d$_6$) δ 3.79 (s, 6H), 7.08 (d, J=8.0 Hz, 1H), 7.21 (d, J=8.8 Hz, 1H), 7.33-7.50 (m, 6H), 7.62 (d, J=8.4 Hz, 1H), 8.01 (bd, J=8.8 Hz, 1H), 8.44 (bs, 1H), 11.41 (bs, 1H).

Example 15

4-Methyl-N-[5-(phenyl)-pyridine-2-yl]benzenesulfonamide

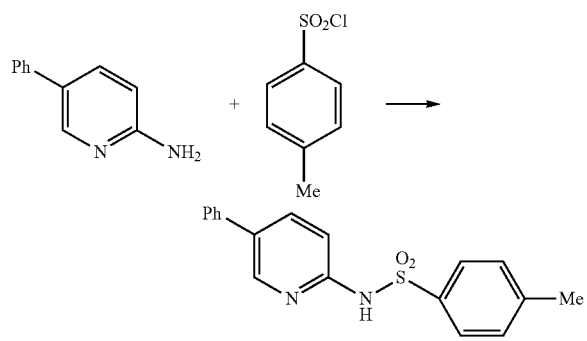

To a solution of 5-phenylpyridin-2-amine (340 mg, 2 mmol) in dry pyridine (10 mL) was added 4-methylbenzenesulfonyl chloride (427 mg, 2.24 mmol). The solution was stirred at room temperature under Argon. The pyridine was then removed in vacuo and flashed off with toluene. The residue was partitioned between EtOAc and 1M NaOH. The organic phase was washed with 1M NaOH until no turbidity was observed on rectification of a small sample. The alkaline phase was made acidic (~pH 3) with 1M HCl and extracted with EtOAc. After drying over Na$_2$SO$_4$, solvent was removed in vacuo. The crude product weighed 0.24 g. The crude product was taken up in 10 mL of hot EtOAc, diluted with 10 mL of hexane and seeded to give 209 mg of white needles with mp 187-189° C.

$^1$H NMR (DMSO d$_6$) δ 2.33 (s, 3H), 7.20 (d, J=8.4 Hz, 1H), 7.32-7.45 (m, 5H), 7.61 (d, J=8.0 Hz, 2H), 7.81 (d, J=8.0 Hz, 2H), 8.01 (bd, J=8.8 Hz, 1H), 8.40 (bs, 1H), 11.65 (bs, 1H).

Example 16

3,4-Dimethoxy-N-[5-(4-chlorophenyl)-1,2,4-thiadiazol-3-yl]benzenesulfonamide

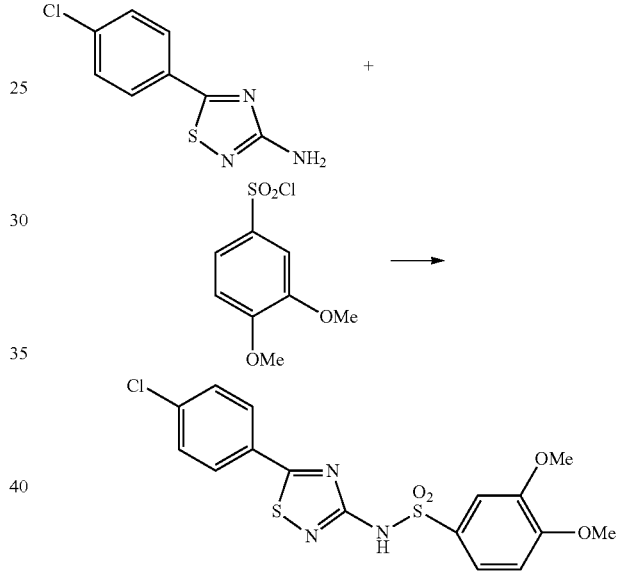

To a solution of 5-(4-chlorophenyl)-1,2,4-thiadiazol-3-amine (423 mg, 2.0 mmol) in 10 mL of dry pyridine was added 529 mg (2.23 mmol) of 3,4-dimethoxybenzenesulfonyl chloride. The solution was stirred at room temperature under Argon. After 21 h, the pyridine was removed in vacuo and flashed off with toluene. The residue was partitioned between EtOAc and 1M NaOH. The organic phase was washed with 1M NaOH until no turbidity was observed on rectification of a small sample. The alkaline phase was made acidic (~pH 3) with 1M HCl and extracted with EtOAc. EtOH was used in the second extraction to assist solubilizing the sulfonamide. After drying over Na$_2$SO$_4$, solvent was removed in vacuo. The crude crystalline product weighed 0.45 g. The crude product was taken up in 13 mL of hot HOAc, diluted with 7 mL of H$_2$O and seeded to give white needles (384 mg) after collection by filtration, washing with H$_2$O, and drying in vacuo. The product had mp 220-221° C.

$^1$H NMR (DMSO d$_6$) δ 3.39 (s, 3H), 3.80 (s, 3H), 7.13 (d, J=8.4 Hz, 1H), 7.51 (d, J=2.0 Hz, 1H), 7.61 (dd, J=2.0, 8.4 Hz, 1H), 7.62 (d, J=8.4 Hz, 2H), 7.91 (d, J=8.4 Hz, 2H), 12.22 (bs, 1H)

$^{13}$C NMR (DMSO d$_6$) δ 55.735, 55.834, 110.211, 111.054, 121.579, 128.117, 128.732, 129.651, 131.033, 137.176, 148.247, 152.606, 162.106, 180.261.

Example 17

3,4-Dimethoxy-N-[biphenyl-4-yl]benzenesulfonamide

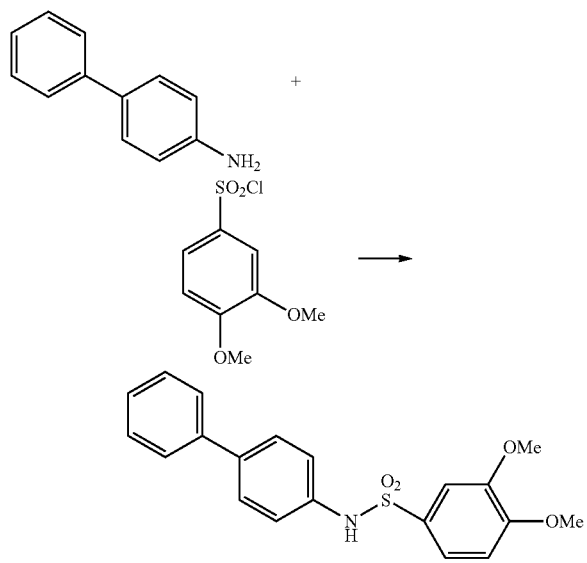

To a solution of biphenyl-4-amine (338 mg, 2 mmol) in 10 mL of dry pyridine followed by 529 mg of 3,4-dimethoxybenzenesulfonyl chloride. The solution was stirred at room temperature under Argon. After 21 h, the pyridine was removed in vacuo and flashed off with toluene. The residue was partitioned between EtOAc and 1M NaOH. The organic phase was washed with 1M NaOH until no turbidity was observed on rectification of a small sample. The alkaline phase was made acidic (~pH 3) with 1M HCl and extracted with EtOAc. After drying over Na$_2$SO$_4$, solvent was removed in vacuo. The crude product (0.79 g) was obtained as a glass which slowly crystallized. Addition of hexane caused complete solidification. The solid was taken up in EtOAc (11 mL), diluted with hexane (11 mL) and seeded to give 534 mg of white needles. The product had mp 171-173° C.

$^1$H NMR (DMSO d$_6$) δ 3.74 (s, 3H), 3.77 (s, 3H), 7.05 (d, J=8.5 Hz, 1H), 7.18 (d, J=8.8 Hz, 2H), 7.27 (d, J=2.0 Hz, 1H), 7.30 (t, J=7.2 Hz, 1H), 7.35 (dd, J=2.0, 8.5 Hz, 1H), 7.40 (t, 2H), 7.54 (d, J=8.8 Hz, 2H), 7.56 (d, J=8.0 Hz, 2H), 10.19 (bs, 1H).

Example 18

3,4-Dimethoxy-N-[5-(3-nitrophenyl)-1,2,4-triazol-3-yl]benzenesulfonamide

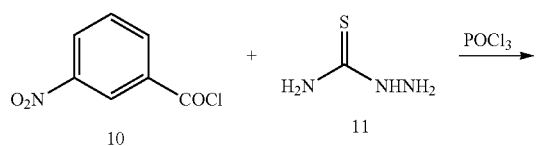

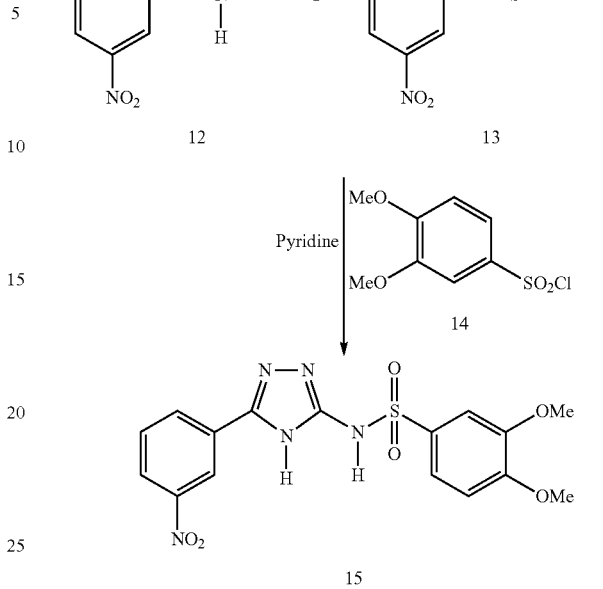

Step 1: 3-Nitrobenzoyl chloride (10, 1.00 g, 5.39 mmol) and thiosemicarbazide (11, 0.49 g, 5.39 mmol) were added to phosphorus oxychloride (15 mL) and the mixture was heated at reflux temperature for 3 h. The reaction mixture was carefully poured into cold water and the precipitated solid was collected by filtration, washed with ether and dried in vacuo to give a mixture of the aminotriazole 12 and the thiadiazole 13, which was used as such for the preparation of 15.

Step 2: 3,4-Dimethoxybenzenesulfonyl chloride (14, 0.260 g, 1.13 mmol) was added to a stirred solution of the above mixture of 12 and 13 (0.500 g) at room temperature and in a nitrogen atmosphere. After 8 h, the reaction mixture was diluted with toluene and then the solvents were removed in vacuo. The residue was partitioned between ethyl acetate and water, the organic phase was dried over anhydrous sodium sulfate, and the solvent was removed in vacuo to give a solid (0.120 g).

$^1$H NMR (CD$_3$OD) δ 3.93 (s, 6H), 6.64 (s, 1H), 7.10 (d, 1H, J=8.8 Hz), 7.42 (bs, 1H), 7.56 (d, 1H, J=8.1 Hz), 7.81 (t, 1H, J=7.5 Hz), 8.23 (d, 1H, J=7.5 Hz), 8.41 (d, 1H, J=7.5 Hz), 8.69 (bs, 1H); MS-ESI m/e 423 (MH)$^+$.

Example 19

4-Methyl-N-[5-(3-nitrophenyl)-1,2,4-triazol-3-yl]benzenesulfonamide

Same procedure as example 21 except that 4-methylbenzenesulfonyl chloride is used instead of 3,4-dimethoxybenzenesulfonyl chloride.

Compound is a white solid. $^1$H NMR (CD$_3$OD) δ 2.45 (s, 3H), 7.42 (d, 2H, J=8.8 Hz), 7.82 (t, 1H, J=7.9 Hz), 7.84 (d, 2H, J=8.8 Hz), 8.24 (d, 1H, J=8.1 Hz), 8.43 (d, 1H, J=7.7 Hz), 8.70 (bs, 1H); MS-ESI m/e 377 (MH)$^+$.

Analogously, following compounds in the Table were also prepared:

| Compound | Compound name |
|---|---|
| A3 | 3,4-dimethoxy-N-[3-(3-nitrophenyl)-1,2,4-thiadiazole-5-yl]benzenesulfonamide |
| A4 | 4-methyl-N-[3-(3-nitrophenyl)-1,2,4-thiadiazole-5-yl[benzenesulfonamide |
| A5 | 3,4-dimethoxy-N-[5-(phenyl)-1,3,4-thiadiazol-2-yl]benzenesulfonamide |
| A6 | 4-methyl-N-[5-(phenyl)-1,3,4-thiadiazol-2-yl]benzenesulfonamide |
| A7 | 3,4-dimethoxy-N-[5-(3-nitrophenyl)-1,3,4-thiadiazole-2-yl]benzenesulfonamide |
| A8 | 4-methyl-N-[5-(3-nitrophenyl)-1,3,4-thiadiazole-2-yl]benzenesulfonamide |
| A11 | 3,4-Dimethoxy-N-[5-(3-nitrophenyl)-1,2,4-triazol-3-yl]benzenesulfonamide |
| A12 | 4-Methyl-N-[5-(3-nitrophenyl)-1,2,4-triazol-3-yl]benzenesulfonamide |
| A20 | 3,4-dimethoxy-N-[5-(3-nitrophenyl)-1,2,4-thiadiazole-3-yl]benzenesulfonamide |
| A21 | 3,4-dimethoxy-N-[5-(phenyl)-1,2,4-thiadiazole-3-yl]benzenesulfonamide |

From the foregoing it will be appreciated that, although specific embodiments of the invention have been described herein for purposes of illustration, various modifications may be made without deviating from the spirit and scope of the invention.

What is claimed is:

1. A method for inhibiting activity of kynurenine-3-monooxygenase which method comprises contacting a cell in need of inhibition of kynurenine-3-monooxygenase activity with an effective amount of one or more compounds of Formula II:

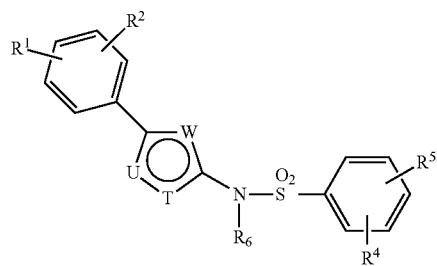

wherein:

T and W independently are selected from the group consisting of N, $NR^3$, S, S(O), $S(O)_2$, O, and $CR^3$ and U is selected from the group consisting of N, $NR^3$, S, S(O), $S(O)_2$, and O with the proviso that no more than one of T, U, and W are S, S(O), $S(O)_2$, and O;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, alkyl, substituted alkyl, alkoxy, substituted alkoxy, halo, amino, substituted amino, alkylthio, substituted alkylthio, substituted sulfonyl, substituted sulfinyl, aryl, substituted aryl, heteroaryl, and substituted heteroaryl;

$R^4$ and $R^5$ are independently selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl; and $R^6$ is selected from the group consisting of hydrogen, alkyl, substituted alkyl, aryl, substituted aryl, heteroaryl, and substituted heteroaryl;

or its tautomer and/or a pharmaceutically acceptable salt thereof, with the proviso that the ring comprising U, W, and T is not 1,3-thiazol-2-yl.

2. The method according to claim 1, wherein the group

is thiadiazole.

3. The method according to claim 1 wherein the compound is of Formula IIa or its tautomer and/or a pharmaceutically acceptable salt thereof:

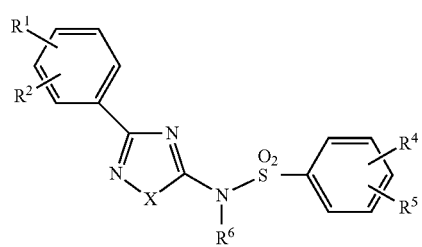

wherein X is S or $NR^9$ where $R^9$ is alkyl or substituted alkyl; and $R^1$, $R^2$, $R^4$, $R^5$, and $R^6$ are as defined in claim 1.

4. The method according to claim 3, wherein $R^1$ and $R^2$ independently are selected from the group consisting of hydrogen, nitro, trifluoromethyl, cyano, and halo.

5. The method according to claim 3, wherein $R^4$ and $R^5$ independently are selected from the group consisting of hydrogen, alkyl, substituted alkyl, alkoxy, and substituted alkoxy.

6. The method according to claim 3, wherein $R^6$ is hydrogen.

7. The method according to claim 1 wherein the compound is of Formula IIb or its tautomer and/or a pharmaceutically acceptable salt thereof:

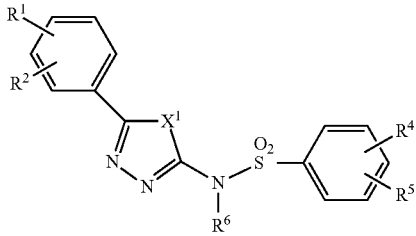

IIb wherein $X^1$ is S or NH; and $R^1$, $R^2$, $R^4$, $R^5$, and $R^6$ are as defined in claim 1.

8. The method according to claim 7, wherein $R^1$ and $R^2$ independently are selected from the group consisting of hydrogen, nitro, trifluoromethyl, cyano, and halo.

9. The method according to claim 7, wherein $R^4$ and $R^5$ independently are selected from the group consisting of hydrogen, alkyl, substituted alkyl, alkoxy, and substituted alkoxy.

10. The method according to claim 7, wherein $R^6$ is hydrogen.

11. The method according to claim 1 wherein the compound is of Formula IIc or its tautomer and/or a pharmaceutically acceptable salt thereof:

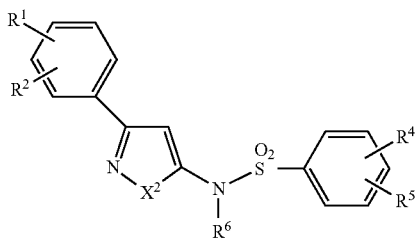

IIc wherein $X^2$ is O or $NR^9$ where $R^9$ is alkyl or substituted alkyl; and $R^1$, $R^2$, $R^4$, $R^5$, and $R^6$ are as defined in claim 1.

12. The method according to claim 1 wherein the compound is of Formula IId or its tautomer and/or a pharmaceutically acceptable salt thereof:

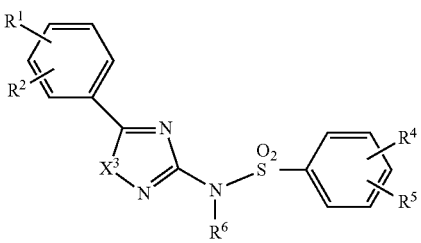

IId wherein $X^3$ is S or $NR^9$ where $R^9$ is alkyl or substituted alkyl; and $R^1$, $R^2$, $R^4$, $R^5$, and $R^6$ are as defined in claim 1.

13. The method according to claim 12, wherein $R^1$ and $R^2$ independently are selected from the group consisting of hydrogen, nitro, trifluoromethyl, cyano, and halo.

14. The method according to claim 12, wherein $R^4$ and $R^5$ independently are selected from the group consisting of hydrogen, alkyl, substituted alkyl, alkoxy, and substituted alkoxy.

15. The method according to claim 12, wherein $R^6$ is hydrogen.

16. The method according to claim 1, where in the compound is selected from the group consisting of 3,4-dimethoxy-N-[3-phenyl-1,2,4-thiadiazol-5-yl]benzenesulfonamide;

4-methyl-N-[3-phenyl-1,2,4-thiadiazol-5-yl]benzenesulfonamide;

3,4-dimethoxy-N-[3-(3-nitrophenyl)-1,2,4-thiadiazol-5-yl]benzenesulfonamide;

4-methyl-N-[3-(3-nitrophenyl)-1,2,4-thiadiazol-5-yl]benzenesulfonamide;

3,4-dimethoxy-N-(1-methyl-3-phenyl-1,2,4-triazol-5-yl)benzenesulfonamide;

4-methyl-N-(1-methyl-3-phenyl-1,2,4-triazol-5-yl)benzenesulfonamide;

3,4-dimethoxy-N-[3-(phenyl)-1,2,4-triazol-5-yl]benzenesulfonamide;

4-methyl-N-[3-(phenyl)-1,2,4-triazol-5-yl]benzenesulfonamide;

3,4-dimethoxy-N-[3-(3-nitrophenyl)-1,2,4-triazol-5-yl]benzenesulfonamide;

4-methyl-N-[3-(3-nitrophenyl)-1,2,4-triazol-5-yl]benzenesulfonamide;

3,4-dimethoxy-N-[5-(phenyl)-1,3,4-thiadiazol-2-yl]benzenesulfonamide;

4-methyl-N-[5-(phenyl)-1,3,4-thiadiazol-2-yl]benzenesulfonamide;

3,4-dimethoxy-N-[5-(3-nitrophenyl)-1,3,4-thiadiazol-2-yl]benzenesulfonamide;

4-methyl-N-[5-(3-nitrophenyl)-1,3,4-thiadiazol-2-yl]benzenesulfonamide;

3,4-dimethoxy-N-[3-(phenyl)-isoxazol-5-yl]benzenesulfonamide;

4-methyl-N-[3-(phenyl)-isoxazol-5-yl]benzenesulfonamide;

3,4-dimethoxy-N-[1-methyl-3-phenyl-pyrazol-5-yl]benzenesulfonamide;

4-methyl-N-[1-methyl-3-phenyl-pyrazol-5-yl]benzenesulfonamide;

3,4-dimethoxy-N-[5-(4-chlorophenyl)-1,2,4-thiadiazole-3-yl]benzenesulfonamide;

3,4-dimethoxy-N-[5-(3-nitrophenyl)-1,2,4-thiadiazole-3-yl]benzenesulfonamide; and 3,4-dimethoxy-N-[5-(phenyl)-1,2,4-thiadiazole-3-yl]benzenesulfonamide.

17. A method for inhibiting activity of kynurenine-3-monooxygenase which method comprises contacting a cell with an effective amount of one or more compounds of Formula IIb:

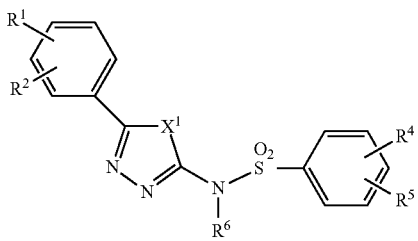

wherein $X^1$ is S;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl;

$R^3$ is selected from the group consisting of hydrogen, alkyl, substituted alkyl, alkoxy, substituted alkoxy, halo, amino, substituted amino, alkylthio, substituted alkylthio, substituted sulfonyl, substituted sulfinyl, aryl, substituted aryl, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl; and $R^6$ is selected from the group consisting of hydrogen, alkyl, substituted alkyl, aryl, substituted aryl, heteroaryl, and substituted heteroaryl;

or a tautomer and/or a pharmaceutically acceptable salt thereof.

* * * * *